United States Patent [19]

Sorge et al.

[11] Patent Number: 5,599,921
[45] Date of Patent: Feb. 4, 1997

[54] OLIGONUCLEOTIDE FAMILIES USEFUL FOR PRODUCING PRIMERS

[75] Inventors: Joseph A. Sorge, Rancho Santa Fe; Dan Shoemaker, Del Mar; Michael Weiner, San Diego, all of Calif.

[73] Assignee: Stratagene, La Jolla, Calif.

[21] Appl. No.: 697,936

[22] Filed: May 8, 1991

[51] Int. Cl.⁶ .......................... C07H 21/00; C07H 21/04
[52] U.S. Cl. ............................................. 536/24.33; 435/6
[58] Field of Search ................................. 536/27, 24, 33; 435/6; 935/77

[56] References Cited

FOREIGN PATENT DOCUMENTS 8911211  11/1989  WIPO.

OTHER PUBLICATIONS

Ausubel et al., "Current Protocols in Molecular Biology", Suppl. 13. pp. 8.1.1–8.4.7, Johen Wiley & Sons, Inc., N.Y. (1991).

Landegren et al., *Science*, 241:1077–1080 (1988).

Studier, Proc. Natl. Acad. Sci 86:6917–6921, 1989.

Szybalski, Gene. 90:177–178, 1990.

*Primary Examiner*—Gary L. Kunz
*Attorney, Agent, or Firm*—Albert P. Halluin, Esq.; Pennie & Edmunds

[57] ABSTRACT

A composition comprising a family of oligonucleotides all of the same length, said family defined by a nucleotide sequence formula containing six to eight nucleotide positions, one to three of said positions of the formula identifying positions of nucleotide variation among the family members, the remaining nucleotide positions each identifying a nucleotide that is the same in all members of the family.

15 Claims, 6 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CTGGCCGTCG       10

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

ACTGGCCGTC GT       12

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TCACTGGCCG TCGTTT       16

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TCGCTGGCCG TCGGTT 16

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TCACTGGCCG TCGATT 16

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TCCCTGGCCG TCGCTT 16

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

TCGCTGGCCG TCGGTT 16

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TCTCTGGCCG TCGTTT 16

( 2 ) INFORMATION FOR SEQ ID NO:9:

( i ) SEQUENCE CHARACTERISTICS:

(A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TCACTNGCCG TNGTTT     16

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCAGCATGGA TT     12

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TCACTTAGAC CG     12

OLIGONUCLEOTIDE FAMILIES USEFUL FOR PRODUCING PRIMERS

TECHNICAL FIELD

The present invention relates to families of oligonucleotides, preferably hexamers, defined by a nucleotide sequence having a predetermined number of constant and variable positions, the constant positions defining a sequence conserved among the members of the family.

BACKGROUND

Oligonucleotides are widely utilized in molecular biological manipulations including DNA sequencing, in vitro mutagenesis, cloning methodologies involving polylinkers and adapters, synthesis of genes by hybridization and ligation of multiple oligonucleotides, and the like methods. Traditionally, oligonucleotides are prepared by chemical synthesis methods de novo each time they are required.

For DNA sequencing, unique oligonucleotide sequencing primers are required as each new sequence is identified. Chemical synthesis of oligonucleotides is time consuming and custom synthesis is costly.

Recently, Studier proposed a strategy to simplify the preparation of unique oligonucleotides in the form of a library of pre-synthesized oligonucleotides representing every possible nucleotide sequence in the size range of oligonucleotides from 8 to 10 nucleotides in length. Studier, *Proc.Natl.Acad.Sci.USA*, 86:6917–6921 (1989). The library poses technical difficulties insofar as the library must contain from $4^8$ (65,536) to $4^{10}$ (1,048,576) members, respectively, which is generally considered to be so large as to be unmanageable.

Szybalski proposed the use of a library of hexameric oligonucleotides comprising every possible combination of nucleotide bases, representing a library having $4^6$ (4,096) members. Szybalski, *Gene*, 90:177–178 (1990). Theoretically, the hexamers in the library were proposed to be capable of being individually ligated to form 12 nucleotide (nt), 18-nt, or 24-nt oligonucleotides in length, therefore forming every possible nucleotide sequence from a library having 4,096 members.

However, it has not been shown that hexamers can actually be used to form 12-nt long sequencing primers.

BRIEF SUMMARY OF THE INVENTION

It has now been discovered that a collection of oligonucleotides having related, but distinct sequences, can be simultaneously mixed with a template, oligonucleotides complementary to the template can hybridize and, if adjacent, can be ligated to form sequencing primers.

The present invention contemplates a composition comprising a family of oligonucleotides all of the same length, said family defined by a nucleotide sequence formula containing six to eight nucleotide positions, one to three of said positions of the formula identifying positions of nucleotide variation among the family members, the remaining nucleotide positions each identifying a nucleotide that is the same in all members of the family.

Also contemplated is a composition comprising a family of oligonucleotides comprising hexameric oligonucleotides, each family member having a nucleotide sequence that is different from the other family members, the family defined by a nucleotide sequence formula containing four constant and two variable positions, each constant position identifying, independent of the other constant positions, a nucleotide that is the same in all family members.

Further contemplated is a composition comprising a family of template oligonucleotides 12 to 200 nucleotides in length, each member of the family containing a primer synthesis site ten nucleotides in length having a nucleotide sequence formula containing eight constant and two variable positions, said site being flanked at each terminus by at least one nucleotide.

A composition comprising a family of template oligonucleotides is also contemplated. The family members are all of the same length, the length being 12 to 200 nucleotides in length, each member of the family containing a nucleotide sequence according to the formula:

wherein X and Y are each the same for all family members and represent nucleotide sequences having a length corresponding to the value of a and b, respectively, with the proviso that a and b are whole integers from 0 to 8 such that the sum of a+b is 8, $N_1$ and $N_2$ are individual nucleotides that vary between family members, and c is a whole integer from 2 to 20 indicating the number of times the bracketed sequence is present in a family member.

A kit for producing a dodecameric oligonucleotide of preselected priming specificity are also contemplated. The kit comprises a plurality of separate packages within an enclosure, each package containing a different hexameric oligonucleotide composition, said composition comprising a family of hexameric oligonucleotide composition, said composition comprising a family of hexameric oligonucleotides, each family member having a nucleotide sequence that is different from the other family members, the family defined by a nucleotide sequence formula containing four constant and two variable positions, each constant position identifying, independent of the other constant positions, a nucleotide that is the same in all family members, the hexameric oligonucleotides of each composition being adapted for ligation to any one of the hexameric oligonucleotides in each of the other packages to produce said dodecameric oligonucleotide.

DETAILED DESCRIPTION OF THE INVENTION

A. Definitions

Figure 1:
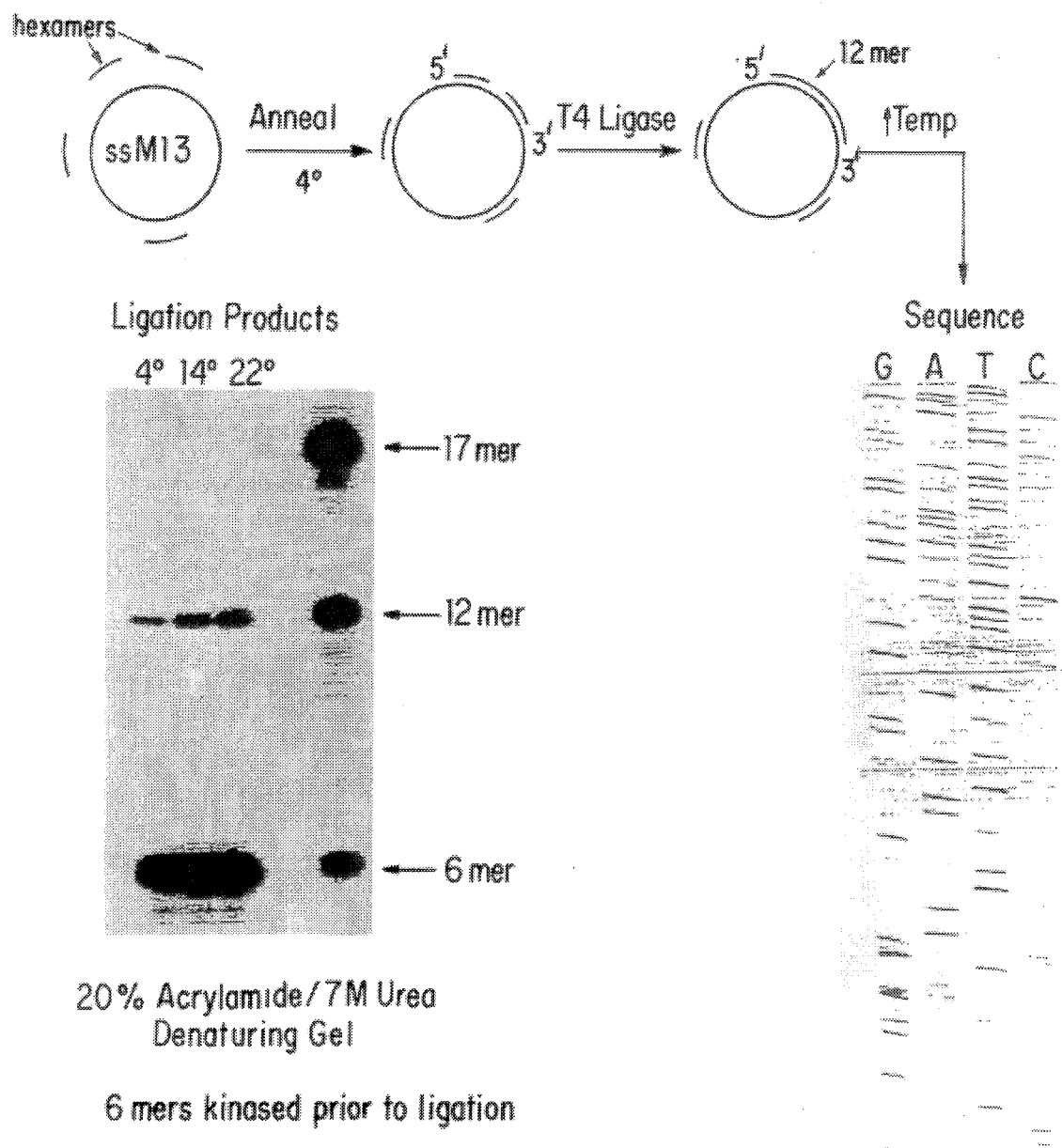
FIG. 1 illustrates ligation of two hexamers to single-stranded M13mp7 in preparation for sequencing as described in Example 2. The schematic diagram at the top of the figure illustrates the steps used to ligate the hexamer while hybridized to template. The gel (20% acrylamide/7M urea) photograph in the lower left portion of the figure demonstrates that the hexamer will ligate to form a 12-mer at 4C, 14C, and 22C. The 6-, 12- and 17-mer bands in the far right lane are oligonucleotide standards. The sequencing gel shown in the lower right portion of the figure demonstrates high resolution sequencing of M13mp7 using ligated hexamers.

Common Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. Common nucleotides are adenine, thymine, cytosine, guanine and uracil.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded.

Polynucleotide: The term "polynucleotide" as used herein in reference to primers, probes and nucleic acid fragments or segments to be synthesized by ligation of oligonucleotides or by primer extension is defined as a molecule comprised of two or more deoxyribonucleotides or ribonucleotides, preferably more than 3. Its exact size will depend on many factors, which in turn depends on the ultimate conditions of use.

Gene: A nucleic acid whose nucleotide sequence codes for an RNA or polypeptide. A gene can be either RNA or DNA.

Complementary Bases: Nucleotides that normally pair up when DNA or RNA adopts a double stranded configuration.

Complementary Nucleotide Sequence: A sequence of nucleotides in a single-stranded molecule of DNA or RNA that is sufficiently complementary to that on another single strand to specifically hybridize to it with consequent hydrogen bonding.

Conserved: A nucleotide sequence is conserved with respect to a preselected (reference) sequence if it non-randomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

Nucleotide Analog: A purine or pyrimidine nucleotide that differs structurally from A, T, G, C, or U, but is sufficiently similar to substitute for the normal nucleotide in a nucleic acid molecule.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Reading Frame: Particular sequence of contiguous nucleotide triplets (codons) employed in translation. The reading frame depends on the location of the translation initiation codon.

B. Oligonucleotide Compositions

The present invention contemplates a family of oligonucleotides, in admixture. The family members are all of the same length, which is about six to eight nucleotides. The family is defined by a nucleotide sequence represented by a formula containing 6, 7 or 8 nucleotide positions. One, two or three of the nucleotide positions are occupied by nucleotides that vary in type, e.g., A, T, G, C, or U, at that position among the family members. The remaining nucleotide positions of the sequence are each occupied by a nucleotide that is the same at that position, in all members of the family.

Exemplary preferred embodiments are families of hexamers, heptamers or octamers defined by a nucleotide sequence having two variable positions. In these embodiments, all family members contain a conserved sequence, i.e., a sequence that is the same in all family members. Preferably, the variable positions are adjacently located, i.e., are next to each other, in the sequence, more preferably at either the 5'- or 3'-terminus of the oligonucleotide.

In preferred embodiments, the oligomeric nucleotides (oligomers) are adapted for ligation to another nucleotide, such as a terminal oligonucleotide of another oligomer. Such adaptation is typically in the form of a 5'-terminal phosphate to permit enzymatic ligation. A useful phosphorylating reaction 30 microliters of a reaction buffer containing 50 mM Tris-HCl, pH 7.5, 10 mM $MgCl_2$, 5 mM DTT, 1 to 10 micrograms of oligonucleotide, 1 mM ATP, 50 micrograms of bovine serum albumin and 20 units of bacteriophage T4 polynucleotide kinase. Incubate at 37° C. for 60 minutes. Stop the reaction by adding 1 μl of 0.5M EDTA. If desired, [gamma-32p]ATP can be added to the reaction to produce labeled oligonucleotide.

In further embodiments, at least one, and preferably two, of the nucleotides occupying constant positions in the nucleotide sequence are selected from the group consisting of cytosine (C) and guanine (G). It is also preferred that less than half of the nucleotides occupying the constant positions of the nucleotide sequence are selected from the group consisting of adenine (A) and thymine (T).

Usually, each of the family members are present in the composition in relative molar amounts such that any one member is present at no more than a ten-fold excess, and preferably no more than a five-fold excess, over the amount of the least abundant member. Most preferably, all of the family members are present in about equal molar amounts.

The family members can be labeled, i.e., operatively linked to an indicating means or group, and used to detect the presence of a specific nucleotide sequence in a target template.

Detecting the presence of a DNA duplex in a process of the present invention can be accomplished by a variety of means.

In one approach for detecting the presence of a DNA duplex, a family member that is hybridized in the DNA duplex includes a label or indicating group that will render the duplex detectable. Typically such labels include radioactive atoms, chemically modified nucleotide bases, and the like.

Radioactive elements operatively linked to or present as part of a oligonucleotide probe (labeled family member) provide a useful means to facilitate the detection of a DNA duplex. A typical radioactive element is one that produces beta ray emissions. Elements that emit beta rays, such as 3H, 14C, 32P and 35S represent a class of beta ray emission-producing radioactive element labels. A radioactive polynucleotide probe is typically prepared by enzymatic incorporation of radioactively labeled nucleotides into a nucleic acid using DNA kinase.

Alternatives to radioactively labeled oligonucleotides are oligonucleotides that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or oligonucleotide via a chelate forming compound such as an EDTA-analogue so that a fluorescent lanthanide complex is formed. See U.S. Pat. No. 4,374,120, No. 4,569,790 and published Patent Application Nos. EP0139675 and WO87/02708.

Biotin or acridine ester-labeled oligonucleotides and their use to label polynucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled oligonucleotide present in a DNA duplex renders the duplex itself labeled and therefore distinguishable over other nucleic acids present in a sample to be assayed. Detecting the presence of the label in the duplex and thereby the presence of the duplex, typically involves separating the DNA duplex from any labeled oligonucleotide probe that is not hybridized to a DNA duplex.

Techniques for the separation of single stranded oligonucleotide, such as non-hybridized labeled oligonucleotide probe, from DNA duplex are well known, and typically involve the separation of single stranded from double stranded nucleic acids on the basis of their chemical properties. More often separation techniques involve the use of a heterogeneous hybridization format in which the nonhybridized probe is separated, typically by washing, from the DNA duplex that is bound to an insoluble matrix. Exemplary is the Southern blot technique, in which the matrix is a nitrocellulose sheet and the label is 32P. Southern, *J. Mol. Biol.*, 98:503 (1975).

The family members can also be advantageously linked, typically at or near their 5'-terminus, to a solid matrix, i.e., aqueous insoluble solid support. Useful solid matrices are well known in the art and include cross-linked dextran such as that available under the tradename SEPHADEX from Pharmacia Fine Chemicals ()Piscataway, NJ); agarose, polystyrene or latex beads about 1 micron to about 5 mm in diameter, polyvinyl chloride, polystyrene, cross-linked polyacrylamide, nitrocellulose or nylon-based webs such as sheets, strips, paddles, plates microtiter plate wells and the like.

In preferred embodiment, the nucleotide sequence formula of the oligomer, read from left to right and in the direction of 5'-terminus to 3'-terminus, is:

$N_1X_1X_2X_3X_4N_2$, wherein $X_1$, $X_2$, $X_3$, and $X_4$ are the same or different nucleotide located at said four constant positions, and $N_1$ and $N_2$ are the same or different nucleotide located at said two variable positions.

In another preferred embodiment, the nucleotide sequence formula of the oligomer, read from left to right and in the direction of 5'-terminus to 3'-terminus, is selected from the group consisting of:

(a) $N_1\ X_1\ X_2\ X_3\ X_4\ N_2$,
(b) $N_1\ N_2\ X_1\ X_2\ X_3\ X_4$, and
(c) $X_1\ X_2\ X_3\ X_4\ N_1\ N_2$, wherein $X_1$, $X_2$, $X_3$ and $X_4$ are the same or different nucleotide located at said four constant positions, and $N_1$ and $N_2$ are the same or different nucleotide located at said two variable positions.

Also contemplated are compositions where the nucleotide sequence formula of the oligomer, read from left to right and in the direction of 5'-terminus to 3'-terminus, is selected from the group consisting of:

(a) $N_1\ X_1\ N_2\ X_2\ X_3\ X_4$,
(b) $N_1\ X_1\ X_2\ N_2\ X_3\ X_4$,
(c) $N_1\ X_1\ X_2\ X_3\ N_2\ X_4$,
(d) $X_1\ N_1\ N_2\ X_2\ X_3\ X_4$,
(e) $X_1\ N_1\ X_2\ N_2\ X_3\ X_4$,
(f) $X_1\ N_1\ X_2\ X_3\ N_2\ X_4$,
(g) $X_1\ N_1\ X_2\ X_3\ X_4\ N_2$,
(h) $X_1\ X_2\ N_1\ N_2\ X_3\ X_4$,
(i) $X_1\ X_2\ N_1\ X_3\ N_2\ X_4$,
(j) $X_1\ X_2\ N_1\ X_3\ X_4\ N_2$,
(k) $X_1\ X_2\ X_3\ N_1\ N_2\ X_4$, and
(l) $X_1\ X_2\ X_3\ N_1\ X_4\ N_2$, wherein $X_1$, $X_2$, $X_3$ and $X_4$ are the same or different nucleotide located at said four constant positions, and $N_1$ and $N_2$ are the same or different nucleotide located at said two variable positions.

Further contemplated is a composition comprising a family of oligonucleotides comprising hexameric oligonucleotides, each family member having a nucleotide sequence that is different from the other family members, the family defined by a nucleotide sequence formula containing five constant and one variable positions, each constant position identifying, independent of the other constant positions, a nucleotide that is the same in all family members. Preferably, the nucleotide sequence formula, read from left to right and in the direction of 5'-terminus to 3'-terminus, is selected from the group consisting of:

(a) $N_1\ X_1\ X_2\ X_3\ X_4\ X_5$, and
(b) $X_1\ X_2\ X_3\ X_4\ X_5\ N_1$, wherein $X_1$, $X_2$, $X_3$, $X_4$ and $X_5$ are the same or different nucleotides located at said five constant positions, and $N_1$ is a nucleotide located at said one variable position.

In another preferred hexameric composition the nucleotide sequence formula, read from left to right and in the direction of 5'-terminus to 3'-terminus, is selected from the group consisting of:

(a) $X_1\ N_1\ X_2\ X_3\ X_4\ X_5$, (b) $X_1\ X_2\ N_1\ X_3\ X_4\ X_5$, (c) $X_1\ X_2\ X_3\ N_1\ X_4\ X_5$, and (d) $X_1\ X_2\ X_3\ X_4\ N_1\ X_5$, wherein $X_1$, $X_2$, $X_3$, $X_4$ and $X_5$ are the same or different nucleotides located at said five constant positions, and $N_1$ is a nucleotide located at said one variable position.

Increasing the G and/or C content of the hexamer can improve its hybridization characteristics. Thus, preferred hexamer compositions include those having a nucleotide formula, read from left to right and in the direction of 5'-terminus to 3'-terminus, is selected from the group consisting of:

(a) $N_1\ X_1 X_2\ X_3\ X_4\ X_5$, and (b) $X_1\ X_2\ X_3\ X_4\ X_5\ N_1$, wherein $X_1$, $X_2$, $X_3$, $X_4$ and $X_5$ are the same or different nucleotide located at said five constant positions, with the proviso that at least two of $X_1$, $X_2$, $X_3$, $X_4$ and $X_5$ are the nucleotides G or C, and $N_1$ is a nucleotide located at said one variable position. Also preferred are compositions where the family of oligonucleotides is represented by the formula:

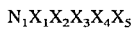

$N_1 X_1 X_2 X_3 X_4 X_5$ wherein $X_4$ and $X_5$ are the nucleotides G or C. Further preferred are compositions where the family of oligonucleotides is represented by the formula:

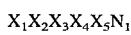

$X_1 X_2 X_3 X_4 X_5 N_1$ wherein $X_1$ and $X_2$ are the nucleotides G or C.

The oligonucleotide compositions of the present invention can be prepared using any suitable method, such as, for example, the phosphotriester or phosphodiester methods see Narang et al., *Meth. Enzymol.*, 68:90, (1979); U.S. Pat. No. 4,356,270; and Brown et al., *Meth. Enzymol.*, 68:109, (1979).

For compositions having a specified family of oligonucleotides as defined herein, synthesis of the family members can be conducted simultaneously in a single reaction vessel, or can be synthesized independently and later admixed in preselected molar ratios.

For simultaneous synthesis, the nucleotide residues that are conserved at preselected positions of the sequence of the family member can be introduced in a chemical synthesis protocol simultaneously to all members in the family by the addition of a single preselected nucleotide precursor to the solid phase oligonucleotide reaction admixture when that position number of the oligonucleotide is being chemically added to the growing oligonucleotide polymer. The addition of nucleotide residues to those positions in the sequence that vary between the members of a family can be introduced simultaneously by the addition of amounts, preferably equimolar amounts, of multiple preselected nucleotide precursors to the solid phase oligonucleotide reaction admixture during chemical synthesis. For example, where all four possible natural nucleotides (A,T,G and C) are to be added at a preselected position, their precursors are added to the oligonucleotide synthesis reaction at that step to simultaneously form four variants within the family.

This manner of simultaneous synthesis of a family of related oligonucleotides has been previously described for the preparation of "degenerate oligonucleotides" by Ausubel et al, in "Current Protocols in Molecular Biology" Suppl. 8. p.2.11.7, John Wiley & Sons, Inc., New York (1991), and can readily be applied to the preparation of the oligonucleotide compositions described herein.

Exemplary synthesis protocols are described in Example 1.

Nucleotide bases other than the common four nucleotides (A,T,G or C), or the RNA equivalent nucleotide uracil (U), can be used in the present invention. For example, it is well known that inosine (I) is capable of hybridizing with A, T and G, but not C.

Thus, where all four common nucleotides are to occupy a single position of a family of oligonucleotides, that is, where the preselected oligonucleotide composition is designed to contain oligonucleotides that can hybridize to four sequences that vary at one position, several different oligonucleotide structures are contemplated. The composition can contain four members, where a preselected position contains A,T,G or C. Alternatively, the composition can contain two members, where a preselected position contains I or C, and has the capacity the hybridize at that position to all four possible common nucleotides. Finally, other nucleotides may be included at the preselected position that have the capacity to hybridize in a non-destabilizing manner with more than one of the common nucleotides in a manner similar to inosine.

By non-destabilizing hybridization is meant that the nucleotide can participate in DNA-DNA or DNA-RNA duplex formation (base pairing) without preventing the ordinary complementary hybridization of adjacent nucleotides in the oligonucleotide that would otherwise hybridize to their complement. Inosine is an example of a non-destabilizing hybridizable nucleotide, with specificity for A, T or G. Other nucleotides having this property can also be used in the present invention.

Thus the present invention describes a composition of oligonucleotides, and particularly a hexameric library in the form of a plurality of compositions comprising families of related hexamers, that solves the problems initially posed by Szybalski, *Gene*, 90:177–178 (1990). By incorporating two variable positions in the hexamer, which can occupy any of the six nucleotide positions in the hexamer, 256 16 member pools represent a library able to form all possible combinations of 12-mer oligonucleotides. As described herein, other mathematical combinations with one or three variable nucleotide positions become apparent based on the development of families of related oligonucleotide sequences. Heptamer and octamer libraries can also be prepared, although for sequencing primers, hexamers having two variable positions are preferred.

C. Methods for Producing a Primed Template

1. General Methods

The present invention describes a method for producing a primed template that can then be used in a variety of methods including sequencing of primed DNA templates, and other primer extension reactions requiring a primed nucleic acid template.

The method comprises the steps of:

a) admixing in a hybridization buffer at least one family of oligonucleotides (oligonucleotide composition) with a DNA template molecule having a sequence predetermined to be complementary to at least two oligonucleotides in said pool to form a hybridization reaction admixture, each oligonucleotide in said family being;

b) maintaining said hybridization reaction admixture under hybridization reaction conditions for a time period sufficient for said template to hybridize to the two oligonucleotides and form a ligation reaction substrate having adjacent ligatable ends provided by said two oligonucleotides;

c) treating said ligation reaction substrate to ligation reaction conditions for a time period sufficient for the adjacent ligatable ends of said two oligonucleotides hybridized to said template to be ligated and form a primed template.

a. Hybridizing Oligonucleotide Compositions to a Template

In one embodiment the present invention contemplates a method for hybridizing at least two oligonucleotides to a target sequence present on a nucleic acid to form a hybridization product. A hybridization reaction mixture is prepared by admixing effective amounts of an oligonucleotide composition of the present invention, a target nucleic acid (i.e., template) and other components compatible with a hybridization reaction.

Target nucleic acid sequences to be hybridized in the present methods can be present in any nucleic acid-containing sample so long as the sample is in a form, with respect to purity and concentration, compatible with a nucleic acid hybridization reaction. Isolation of nucleic acids to a degree suitable for hybridization is generally known and can be accomplished by a variety of means. For instance, nucleic acids can be isolated from a variety of nucleic acid-containing samples including body tissue, such as skin, muscle, hair, and the like, and body fluids such as blood, plasma, urine, amniotic fluids, cerebral spinal fluids, and the like. See, for example, Maniatis et al, *Molecular Cloning: A Laboratory Manual*, Cold Spring Harbor Laboratory (1982); and Ausubel et al, *Current Protocols in Molecules Biology*, John Wiley and Sons (1987).

In a preferred embodiments directed at sequencing DNA molecules, a template is a cloning vector, such as a cosmid, phagemid, lambda derived cloning vector or the like cloning vector capable of accommodating a cloned fragment of DNA, containing the cloned DNA fragment, typically derived from a genome to be sequenced.

The hybridization reaction mixture is maintained in the contemplated method under hybridizing conditions for a time period sufficient for the oligonucleotides having complementarity to the predetermined sequence on the template to hybridize to complementary nucleic acid sequences present in the template to form a hybridization product, i.e., a complex containing oligonucleotide and target nucleic acid.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow one or more oligonucleotides to anneal with the target sequence, to form a nucleic acid duplex. Such time, temperature and pH conditions required to accomplish hybridization depend, as is well known in the art, on the length of the oligonucleotide to be hybridized, the degree of complementarity between the oligonucleotide and the target, the guanidine and cytosine content of the oligonucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are carried out at temperatures from 4 degrees C (4° C.) to 37° C., preferably about 12° C. to about 30° C., more preferably about 22° C., and for time periods from 0.5 seconds to 24 hours, preferably 2 minutes (min) to 1 hour. Exemplary are the conditions described in Example 2.

Hybridization can be carried out in a homogeneous or heterogeneous format as is well known. The homogeneous hybridization reaction occurs entirely in solution, in which both the oligonucleotide and the nucleic acid sequences to be hybridized (target) are present in soluble forms in solution. A heterogeneous reaction involves the use of a matrix that is insoluble in the reaction medium to which either the oligonucleotide, polynucleotide probe or target nucleic acid is bound.

In one embodiment referred to herein as sequencing by hybridization, the family of oligonucleotides is in the solid phase.

Where the nucleic acid containing a target sequence is in a double-stranded (ds) form, it is preferred to first denature the dsDNA, as by heating or alkali treatment, prior to conducting the hybridization reaction. The denaturation of the dsDNA can be carried out prior to admixture with a oligonucleotide to be hybridized, or can be carried out after the admixture of the dsDNA with the oligonucleotide.

The oligonucleotide composition admixed to form the hybridization reaction admixture contains at least two oligonucleotides predetermined to be complementary to a sequence present in the template, such that the resulting hybridization product is a ligation reaction substrate.

As used herein, a ligation reaction substrate consists of two oligonucleotides (oligo A and oligo B) hybridized to adjacent sequences on a template such that there is no gap in nucleotides between the 3' terminus of oligo A and the 5' terminus of oligo B, and at least 5 nucleotides at the 3' terminus of oligo A have perfect complementarity with the template, and at least 5 nucleotides at the 5' terminus of oligo B have perfect complementarity with the template. Thus a ligation reaction substrate contains adjacent ligatable ends (oligonucleotide termini), one at the 3' end of oligo A and one at the 5' end of oligo B (see FIG. 5).

Predetermined complementarity between at least two oligonucleotides in the oligonucleotide composition and the template is achieved in two alternative manners. A sequence in the template DNA may be known, such as where the primer to be formed can hybridize to known vector sequences and initiates primer extension into a region of cloned insert DNA for sequencing purposes, or where previous sequencing has determined a region of nucleotide sequence and the primer is designed to extend from the recently sequenced region into a region of unknown sequence. This latter process has been referred to a "directed sequencing" because each round of sequencing is directed by a primer designed based on the previously determined sequence.

Effective amounts of the two oligonucleotides present in the hybridization reaction admixture are generally well known and are typically expressed in terms of molar ratios between the oligonucleotide to be hybridized and the template. Preferred ratios are hybridization reaction mixtures containing equimolar amounts of the target sequence, oligo A and oligo B. As is well known, deviations from equal molarity will produce hybridization reaction products, although at lower efficiency. Thus although ratios where one or two of the three components (template, oligo A and oligo B) can be in as much as 100 fold molar excess relative to the other component (s), excesses of less than 50 fold, preferably less than 10 fold, and more preferably less the 2 fold are desirable in practicing the invention.

In practicing the methods of the invention, it is therefore important in calculating molar ratios to understand that oligonucleotide compositions of this invention can contain, in the context of a particular template, some oligonucleotides that are complementary to the target and some oligonucleotides that are not complementary. Further, the template may contain regions of complementarity to one oligonucleotide but that region does not also have complementarity to another oligonucleotide in the composition, and therefore that region does not form a ligation reaction substrate.

b. Ligation of Hybridized Oligos to Form Primer

In producing a ligated primer using a template oligonucleotide of this invention, the ligation reaction substrate is treated to ligation reaction conditions for a time period sufficient to form a phosphodiester bond between adjacent ligatable ends, namely between the 3' hydroxyl group at the 3'-terminus of oligo A and the 5' phosphate group at the 5'-terminus of oligo B.

Ligation reaction conditions are generally well known in the art and depend, in part, on the ligase to be used for forming the phosphodiester bond, and on the stability of the ligation reaction substrate.

A preferred ligase is T4 DNA ligase, such as is obtained from *Escherichia coli*, which can be obtained from a variety of commercial vendors.

Stability of the ligation reaction substrate is maintained by preserving hybridization reaction conditions during the manipulations after hybridization and during the ligation reaction. The substrate can vary in stability depending on the length of the hybridized oligonucleotide. For the shorter oligonucleotides contemplated by this invention, for example the hexameric oligonucleotides, it is preferred that hybridization and ligation reaction conditions be conducted below 30 degrees Centigrade (30° C.) and preferably between 4° C. and 22° C.

The resulting ligated primer formed by the action of the ligation reaction conditions on the ligation reaction substrate can be isolated from the template and used as described further herein. The separation of the primer from the template can be accomplished by a variety of means following denaturation which destabilizes the hybridized duplex to form free template and free primer. Exemplary separation methods include size fractionation of the template and the primer on gel sieve chromatography, on polyacrylamide gels and the like sizing methods. Particularly preferred is the use of immobilized templates as described herein in the present methods for producing a ligated primer. The immobilized template allow the release of the ligated primer into the liquid phase, and separation of the template by removal of the solid phase.

The term "primer" as used herein refers to a polynucleotide whether purified from a nucleic acid restriction digest or produced synthetically or preferably is synthesized by the present methods, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on may factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template and are less preferred.

The primers produced by the present methods are selected to be "substantially" complementary to the different strands of each specific sequence to be sequenced, synthesized or amplified. This means that the primer must be sufficiently complementary as to non-randomly hybridize with its respective template strand. Therefore, the primer sequence may or may not reflect the exact sequence of the template. For example, a non-complementary nucleotide fragment can be present at the 5' end of the primer, with the remainder of the primer sequence being substantially complementary to the strand. Alternatively, non-complementary bases or longer sequences can be interspersed into the primer, provided the primer sequence has sufficient complementarily with the sequence of the strand to be sequenced, synthesized or amplified to non-randomly hybridize therewith and thereby form an extension product under polynucleotide synthesizing conditions.

In another embodiment, the present invention contemplates the use of three oligonucleotides, rather than two, to hybridize and form a larger ligation reaction substrate. In this embodiment, suited for producing larger primers, a third oligonucleotide (oligo C) is located 3' relative to oligo B, and all three oligos present adjacent ligatable ends such that the resulting ligated primer comprises the continuous sequence of oligos A, B and C in that order.

2. Use in Directed Sequencing

Directed sequencing is a multi-step process in which a large sequence of nucleotides is determined by the steps of: (1) determining a first region of nucleotide sequence, (2) preparing a sequencing primer based on the downstream (3') region of the determined sequence to design the sequencing primer as to be complementary to the template at that downstream region, (3) determining a second region of nucleotide sequence using the sequencing primer designed from the previously determined sequence in a primer extension-based sequencing procedure (e.g., dideoxy sequencing), and (4) repeating steps (2) and (3) for as many cycles as needed to walk down the entire sequence to be determined. This approach is termed directed sequencing because the choice of primer directs the subsequent sequencing steps and thereby sequentially orders the sequence information obtained. Directed sequencing is typically compared to and preferred over random sequencing methods where the sequence information obtained is not directed in any particular order.

In preferred embodiments for practicing the present methods as applied to directed sequencing, the use of the oligonucleotide compositions provide a particular advantage over previous directed sequencing methods.

For example, using previous techniques, after a region of nucleic acid sequence was determined, a sequencing primer would be required to complete the next "directed" sequencing step. That required primer must be chemically synthesized, which consumes time and the expense of custom oligonucleotide synthesis.

By the present invention, the required sequencing primer can be constructed from a preexisting "library" of oligonucleotide compositions by (1) selecting a nucleotide sequence in the region of the template for designing a directed sequencing primer, (2) selecting one or two oligonucleotide compositions, as needed, to provide two oligonucleotides in the hybridization reaction admixture that have complementarity to the region of the template selected for directed priming, and (3) following the methods herein for admixing the selected compositions with the template, hybridizing the admixture to form the ligation reaction substrate and ligating the substrate to form the primer. In the process of forming the ligated primer, the resulting ligation reaction product is a primed template ready for sequencing without further manipulation. Exemplary is the ligation of hexameric oligonucleotides and sequencing of ssM13 described in Example 2.

Because template specificity and hybridization stringency are improved by the use of longer sequencing primers, a related embodiment contemplates in the present methods the preparation by admixture of a hybridization reaction admixture comprising three oligonucleotides having sequence complementarity to the template such that the resulting ligation reaction substrate contains the template with oligos A, B and C hybridized thereto as described further herein. The resulting ligated primer has a nucleotide sequence that includes oligos A, B and C. Particularly preferred are 18-mer primers formed by the template-directed ligation of three hexamers according to the present methods.

The methods for producing ligated primers can be applied to a variety of methods for manipulating and analyzing nucleic acid molecules, as will be apparent to one skilled in the art.

For example, a ligation reaction product (a primed template) can be used in primer extension reactions to produce primer extension reaction products. After producing the ligation reaction product, the primed template is subjected to a primer extension reaction to form a primer extension reaction product containing the ligated primer. By providing excess amounts, relative to template, of the oligonucleotide compositions of this invention to a hybridization reaction one can cycle through successive rounds comprising (1) hybridization of the oligonucleotides, (2) ligation, (3) primer extension, and (4) denaturation to remove the primer extension product. By doing so the excess oligonucleotides will repeatedly hybridize to the template, form ligated primer and extend to cyclically produce primer extension product. This process is referred to as cycle-extending because repeated primer extension product is formed by cycling through the above steps.

In cycle-extending, the denaturation step is typically a heat treatment manipulation to melt the duplex DNA. Such heat treatment necessitates that the ligase used in the ligation step be heat stable, or that additional ligase be added to each ligation reaction admixture at each cycle.

In addition, the primer extension step in cycle-extending is preferably conducted with a heat stable polymerase as described herein for the polymerase chain reaction (PCR) methods.

In a related embodiment, chain terminators such as are used in dideoxy sequencing reaction can be used in the primer extension step of the above cycle-extending method. This allows the repeated production of sequencing reaction products in a cycle-sequencing method. By including the reagents normally used in a dideoxy sequencing reaction at the primer extension step, one can produce amounts of sequencing reaction product in excess of the amount normally provided after one dideoxy sequencing reaction, thereby increasing the sensitivity of the normal sequencing reaction.

In another related embodiment, the invention contemplates a variant cycle-sequencing method involving a series of two cycles.

In the first cycle, limiting amounts of template, such a cosmid DNA, are treated to successive rounds of (1) hybridization to a pair of oligonucleotides (oligo A and oligo B) to form a ligation reaction substrate, (2) ligation to form a ligation reaction product (i.e., the ligated primer), and (3) denaturation at low temperatures to release the ligated primer from the template. The successive rounds are conducted in the presence of mass excess of oligonucleotide pairs so that at each round of hybridization, oligonucleotide annealing (hybridizing) to template is favored over ligated primer annealing to the same region of the template. A mass excess sufficient to favor oligonucleotide annealing is typically at least a 10 fold excess, preferably a 100 fold excess. The amount of excess will depend on the number of cycles performed that consumes input oligonucleotide. If desired, additional oligonucleotide can be added to the hybridization reaction admixture after each cycle to provide mass excesses of the required oligonucleotides.

In the second cycle of the two-cycle method, cycle sequencing is conducted as described above. Because cycle sequencing requires sequential melting of a sequencing primer at temperatures greater than the temperature for the melting step in the first cycle of this two cycle process, a heat stable polymerase is preferred for the sequencing step.

In this two cycle method, the first set of cycles produces mass quantities of a specific sequencing primer by a series of repeated oligonucleotide ligation cycles, and the second set of cycles produces repeated sequencing reaction products, thereby affording increased sensitivity for sequencing using the oligonucleotide compositions of this invention.

3. Use in PCR Reactions

Polymerase chain reactions (PCR) utilize primer extension primers in a pairwise array as is well known. The PCR reaction, however, consumes mass quantities of the primers as each primer becomes incorporated in the primer extension product at each PCR cycle. Therefore, the present compositions and methods are particularly well suited to solving the problem of PCR primer preparation insofar as the PCR primers can be synthesized by ligation as described herein from pre-existing libraries of oligonucleotides rather than chemically synthesized de novo.

For example, to conduct a PCR reaction on a DNA sequence, one selects the desired PCR primer pair, and determines for each primer, the 3' primer and the 5' primer, which oligonucleotide compositions to select as to form a ligation reaction substrate capable of forming a ligated primer corresponding to each PCR primer, using the present methods. Thereafter, one admixes the selected compositions to form a hybridization reaction admixture having at least two oligonucleotides to form the 3' PCR primer and at least two oligonucleotides to form the 5' PCR primer. The hybridization and ligation steps are performed as described before to form the ligated primers, except in this case the template contains two ligated primers hybridized to it and oriented as PCR primers on the template, ready for the PCR reaction.

Other permutations on PCR reaction methodologies will readily be apparent to one skilled in the art. For example, mass quantities of PCR primers can also be prepared using the oligonucleotide compositions of the present invention in combination with one or more of the template oligonucleotides described herein.

PCR amplification methods are described in detail in U.S. Pat. Nos. 4,683,192, 4,683,202, 4,800,159, and 4,965,188, and at least in several texts including "PCR Technology: Principles and Applications for DNA Amplification" H. Erlich, ed , Stockton Press, New York (1989); and "PCR Protocols: A Guide to Methods and Applications" Innis et al., eds., Academic Press, San Diego, Calif. (1990).

The PCR reaction is performed by mixing the PCR primer pair, preferably a predetermined amount thereof, with the template nucleic acid having the sequence to be amplified, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing an amplified PCR reaction product.

The PCR reaction is performed using any suitable method. Generally it occurs in a buffered aqueous solution, i.e., a PCR buffer, preferably at a pH of 7–9, most preferably about 8. Preferably, a molar excess (for genomic nucleic acid, usually about $10_6$:1 primer:template) of the primer is admixed to the buffer containing the template strand. A large molar excess is preferred to improve the efficiency of the process.

The PCR buffer also contains the deoxyribonucleotide triphosphates dATP, dCTP, dGTP, and dTTP and a polymerase, typically thermostable, all in adequate amounts for primer extension (polynucleotide synthesis) reaction. The resulting solution (PCR admixture) is heated to about 90° C. –100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. An exemplary PCR buffer comprises the following: 50 mM KCl; 10 mM Tris-HCl; pH 8.3; 1.5 mM $MgCl_2$; 0.001% (wt/vol) gelatin, 200 µM dATP; 200 µM dTTP; 200 µM dCTP; 200 µM dGTP; and 2.5 units *Thermus aquaticus* DNA polymerase I (U.S. Pat. No. 4,889,818) per 100 microliters of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nucleic Acid Research*, 17:711–722 (1989). Amplification systems based on transcription have been described by Gingeras et al., in *PCR Protocols, A Guide to Methods and Applications*, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

D. Synthetic Oligonucleotide Templates

1. Template Structures

The present invention contemplates a synthetic oligonucleotide template and compositions containing multiple different synthetic oligonucleotide templates useful for promoting the directed ligation of two or more preselected oligonucleotides to form a ligated primer according to the methods described herein. A synthetic oligonucleotide template, or template oligonucleotide, has a nucleotide sequence from about 12 to about 150 nucleotides in length. The nucleotide sequence comprises as least one primer synthesis site defined by ten continuous nucleotides flanked on each end by at least one nucleotide.

A primer synthesis site was determined by the teachings herein to be the minimum nucleotide sequence to which a ligation event can occur between two oligonucleotides catalyzed by T4 DNA ligase when the oligonucleotides are hybridized to a nucleotide sequence comprising ten continuous nucleotide bases within a template nucleotide sequence having a length of at least 12 nucleotides as described herein. More detailed experimental evidence for the minimum primer synthesis site on a template oligonucleotide is described in Example 3.

Thus, a primer synthesis site within a template oligonucleotide is defined by 10 continuous nucleotides forming a predetermined nucleotide sequence. Preferably, a synthetic template contains multiple overlapping primer synthesis sites, each site defining a nucleotide sequence having homology with a different pair of ligatable oligonucleotides.

In another embodiment, the present invention contemplates a composition comprising a family of template oligonucleotides in admixture, preferably equimolar admixture. Each family member is the same length, usually at least 12 and no more than 200, preferably about 80, nucleotides in length. Each family member contains a primer synthesis site at least 10 nucleotides in length. The polynucleotide synthesis site is preferably represented by the formula:

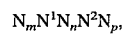

wherein N represents a nucleotide, preferably a common nucleotide, and more preferably a nucleotide selected from the group consisting of A, T, G and C; n, n and p are integers having a value of 0 to 8, inclusive and indicating the number of nucleotides present at each respective positions; and $N^1$ and $N^2$ are single nucleotides; with the proviso that m+n+p=8, the individual nucleotide sequences defined by $N_m$, $N_n$ and $N_p$ are identical for all family members, and $N^1$ and $N^2$ are different among the family members. Preferably, the polynucleotide synthesis site is present in each family member of a plurality of times, such as about 2 to 20, preferably about 10, times, wherein at least one of the sequences $N_m$, $N_n$ and $N_p$ is different each time the sequence is present in a family member.

A pair of ligatable oligonucleotides, in the context of a template oligonucleotide for producing a ligated primer, refers to two oligonucleotides, each at least six nucleotides in length, having a collective nucleotide sequence when aligned by complementarity to a template, and each in the same 5' to 3' orientation direction, such that they define a sequence of ten nucleotides complementary to the sequence of ten nucleotides defining the primer synthesis site of a preselected template oligonucleotide.

For convenience, the first oligonucleotide located 5' relative to the other oligonucleotide in the pair when so aligned will be referred to as "oligo A" and the second oligonucleotide in the pair will be referred to as "oligo B". In this orientation, upon ligation of the pair, the 3' terminus of oligo A is operatively linked by a phosphodiester bond (ligated) to the 5' terminus of oligo B to form the ligated primer.

Following this nomenclature and the teachings herein regarding the minimum "footprint" required for T4 DNA ligase to recognize and ligate a pair of ligatable oligonucleotides, at least the last five 3'-terminal nucleotides of oligo A are complementary and hybridize to the first five nucleotides of the primer synthesis site, and at least the first five 5'-terminal nucleotides of oligo B are complementary and hybridize to the second five nucleotides of the primer synthesis site. This complementarity requirement for a pair of ligatable oligonucleotides to a primer synthesis site is represented diagrammatically in FIG. 5, where nucleotide positions 2 through 12 represent the primer synthesis site on the template oligonucleotide, "A" and "B" represent oligo A and oligo B, respectively, the dotted lines represent hydrogen bonding between hybridizable non-destabilizing nucleotides, and nucleotide positions 1 and 12 represent the position of the additional nucleotides required to define a template oligonucleotide of the present invention.

Thus, a pair of ligatable oligonucleotides is a pair of oligonucleotides each having a preselected sequence that can hybridize to a preselected template oligonucleotide and be ligated by the action of T4 DNA ligase and form a ligated primer according to the methods of this invention.

Figure 5:
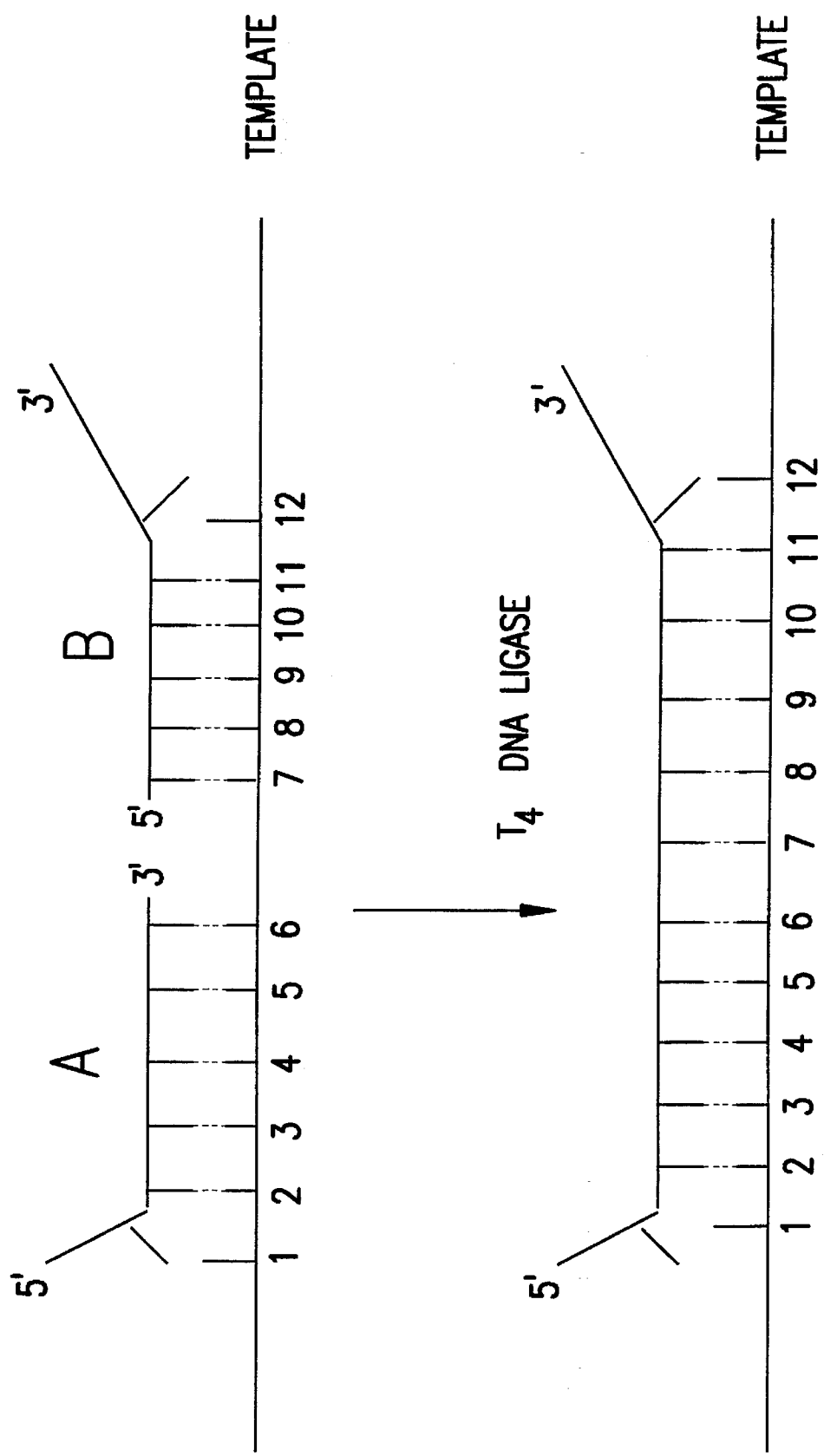
FIG. 5 is a schematic diagram illustrating the minimum primer synthesis site on a template. Oligo A is shown hybridized to the template at positions 2, 3, 4, 5 and 6, and Oligo B is shown hybridized to the template at positions 7, 8, 9, 10 and 11. Nucleotides at position 1 and 12 are shown not hybridized. The dotted lines indicate hydrogen bonding between base pairs. The lower portion of the schematic indicates a ligation reaction product having a phosphodiester bond formed between nucleotides 6 and 7 in the oligo pair.

For template oligonucleotides that define multiple primer synthesis sites that overlap one another, a different primer synthesis site is defined along the length of the template oligonucleotide such that each adjacent nucleotide position may be nucleotide position 1 of each different site in FIG. 5. Thus, for a template oligonucleotide having, for example, 80 nucleotides in length from position 1 to 80, a first primer synthesis site is located at positions 2 through 11, a second site is located at positions 3 through 12, a third site is located at positions 4 through 13, and so on to a 78th site located at positions 70 through 79.

The advantage of such a template oligonucleotide is that a single oligonucleotide can serve as a template for multiple pairs of ligatable oligonucleotides, and can be used according to the methods herein to produce multiple ligated primers using a single reagent. Thus, for example, the above 80-mer template oligonucleotide having a preselected sequence can define 78 different primer synthesis sites and can be used to produce any or all of the different ligated primers that would hybridize to those primer synthesis sites.

As described herein, it has been discovered that compositions containing multiple oligonucleotides, i.e., families of related oligonucleotides, each having a different nucleotide sequence, are useful in the present methods because each family reduces the number of independent oligonucleotide compositions a skilled practitioner must maintain to have represented the full range of possible sequences in any given library of primers.

Thus, the present invention describes a preferred template oligonucleotide composition that comprises a family of template oligonucleotides The oligonucleotide compositions described herein, in particular the libraries of hexamers having 256 16 member pools, or the libraries based on G:C rich hexamers and a single variable position at the 5' terminus of the hexamer, provide a limitation in that the molar amount of template sets an upper limit on the amount of ligated primer that can be made in a single ligation step. Mass amounts of ligated primer are required for such procedures as cycle-sequencing or PCR amplification. Thus the present template oligonucleotide compositions, in particular the libraries of template representing all possible primer synthesis sites, represents a preferred system for producing mass amounts of a specific ligated primer, and more preferably when used in combination with an oligonucleotide composition of this invention.

Based on the teachings herein, a library of about 1000 unique template oligonucleotides, each about 80 nucleotides in length would be sufficient to provide a template for all 16,777,216 possible 12-mer oligonucleotides to be ligated from hexamers by the present methods.

2. Immobilized Templates

In another embodiment a synthetic template according to the present invention can be an immobilized oligonucleotide template that comprises a solid support having affixed thereto one or more species of synthetic templates as described herein.

The solid support can be any of a variety of insoluble materials (i.e., a solid matrix) as is well known, but preferably is a material that can be readily isolated from solid/liquid phase suspensions where the liquid phase is an aqueous solution compatible with a ligation reaction or a hybridization reaction as described herein.

Useful solid matrices are well known in the art. Such materials include the cross-linked dextran available under the trademark SEPHADEX from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The solid support can take the form of a sheet, fibers, granules, beads and the like insoluble forms, with,beads being preferred.

Particularly preferred are the solid support beads upon which the synthetic oligonucleotide chemical synthesis was originally conducted. After oligonucleotide synthesis, the beads are washed in appropriate solvents to provide an aqueous environment so that the beads having the synthetic oligonucleotide affixed thereto are compatible with the hybridization and ligation reactions in which the templates are used.

Methods of affixation of synthetic oligonucleotides to a solid support depends, as is well known, on the type of solid support and the available side groups on the solid support for interaction or reaction with the oligonucleotide to form the immobilized oligonucleotide. The type of linkage between the oligonucleotide and the solid support also depends on the side group available at the termini of the oligonucleotide. Any linkage means is acceptable for practicing the present invention so long as it is stable under the conditions defined herein for hybridization, ligation and denaturation of oligonucleotides hybridized to the template. Exemplary and preferred linkages are of the type typically used to covalently join a synthetic oligonucleotide to the solid support on which it is synthesized. The linkage means may comprise a spacer or linker molecule for connecting the oligonucleotide to the solid support.

In one embodiment, an immobilized template comprises a solid support having multiple oligonucleotides affixed thereto, with the precise number depending on the size of the solid support, each affixed oligonucleotide having the same nucleotide sequence. Such an immobilized template would be useful, for example, in the synthetic template-based methods of the present invention for ligating a particular preselected set of oligonucleotides.

In another embodiment, an immobilized template comprises multiple oligonucleotides such that a population of different nucleotide sequences are represented on each unit of solid support. For example, where the solid support is a bead, each bead may contain several different oligonucleotides or may each contain a large variety of different oligonucleotides, where each different oligonucleotide differs from each other in nucleotide sequence by at least one nucleotide.

In another embodiment, an immobilized template is contemplated that comprises multiple solid support units (e.g., beads) where each unit of solid support contains multiple oligonucleotides each having the same nucleotide sequence, and the oligonucleotide sequence on one or more beads is different. In this embodiment, many different nucleotide sequences can be represented in a preselected fashion by combining solid support units having different oligonucleotides affixed thereto.

Immobilized oligonucleotides can be produced by a variety of synthetic means. Preferred is the synthesis of one or more different oligonucleotides on a bead by the standard solid-phase oligonucleotide chemical synthesis procedures described herein, and then collecting the solid support prior to chemical cleavage normally utilized to release the newly synthesized oligonucleotide from its support.

An immobilized oligonucleotide template is useful in the methods described herein for preparing oligonucleotide primers by the various template-based ligation reactions.

E. Methods for Preparing Oligonucleotide Primers Using Synthetic Oligonucleotide Templates The template oligonucleotides and compositions having a family of templates are useful in methods for preparing primers from an oligonucleotide composition or library of this invention.

Thus the present invention contemplates a method for synthesizing an oligonucleotide primer comprising the steps of:

(1) admixing a template oligonucleotide of this invention with one or more oligonucleotide compositions of this invention that collectively provide at least two oligonucleotides complementary to a primer synthesis site on said template oligonucleotide, to form a hybridization reaction admixture;

(2) subjecting said hybridization reaction admixture to hybridization condition for a time period sufficient for said complementary oligonucleotides to hybridize to said primer synthesis site and form a ligation reaction substrate; and (3) treating said ligation reaction substrate to ligation reaction conditions for a time period sufficient to form a ligated primer.

The hybridization and ligation reaction conditions are performed as previously described. In preferred embodiments the amount of complementary oligonucleotide is an amount in molar excess to the amount of template oligonucleotide, preferably about a 2 to 10 fold excess. Exemplary of the method are the procedures described in Example 3.

A preferred embodiment utilizes an immobilized template oligonucleotide as defined herein. In this method, the template can be conveniently separated from the ligated primer by separation of the liquid phase containing the ligated primer from the solid phase containing the immobilized template. The method has the advantage of convenient reuse of the recovered immobilized template.

F. Kits Using Degenerate Oligonucleotides

Many of the reagents described herein (e.g., nucleic acids such as the oligonucleotide compositions, template oligonucleotide compositions and the like) have a number of forms, particularly variably protonated forms, and in equilibrium with each other. As the skilled practitioner will understand, representation herein of one form of a compound or reagent is intended to include all forms thereof that are in equilibrium with each other.

The reagents described herein can be packaged in kit form. As used herein, the term "package" refers to a solid matrix or material customarily utilized in a system and capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of oligonucleotide compositions, restriction enzyme(s), DNA polymerase, DNA ligase, or a combination thereof. An aliquot of each component sufficient to perform at least one ligation reaction will be provided in each container.

Kits useful for producing a preselected primer for sequencing of a specific nucleic acid sequence or for conducting a PCR amplification reaction using a primer extension reaction methodology also typically include, in separate containers within the kit, dNTPs where N is adenine, thymine, guanine and cytosine, and other like agents for performing primer extension reactions.

The reagent species of any system described herein can be provided in solution, as a liquid dispersion or as a substantially dry powder, e.g., the plasmids may be provided in lyophilized form.

In one embodiment, the present invention contemplates a kit for producing a dodecameric oligonucleotide of preselected priming specificity, which kit comprises a plurality of separate packages within an enclosure, each package containing a different hexameric oligonucleotide composition, said composition comprising a family of hexameric oligonucleotide composition, said composition comprising a family of hexameric oligonucleotides, each family member having a nucleotide sequence that is different from the other family members, the family defined by a nucleotide sequence formula containing four constant and two variable positions, each constant position identifying, independent of the other constant positions, a nucleotide that is the same in all family members, the hexameric oligonucleotides of each composition being adapted for ligation to any one of the hexameric oligonucleotides in each of the other packages to produce said dodecameric oligonucleotide.

A kit can contain a plurality of containers, each container having a different oligonucleotide composition of the present invention. Particularly preferred kits contain a plurality of hexamer compositions that represent all possible combinations of nucleotide sequence for a hexamer. Each family of hexamers is preferably present in a separate container. Kits having a plurality of such compositions are referred to herein as libraries. A preferred library contains 256 separate containers, each containing a different family of hexamers as defined herein.

In another embodiment, a library contains 256 different families of hexamers, each family in a different container, and each family defined herein according to the formula 5'-N $X_1$ $X_2$ $X_3$ $X_4$ $X_5$-3' where $X_4$ and $X_5$ are G or C.

A kit can also contain, in separate containers, a template oligonucleotide or a composition having a family of sequence-related template oligonucleotides as defined herein.

Kits having both libraries of oligonucleotide compositions and template oligonucleotide compositions are also contemplated for practicing the present methods for synthesizing preselected ligated primers.

In addition, a kit can contain an oligonucleotide composition of this invention in an immobilized form. Particularly preferred are kits having a solid support where each family of oligonucleotides are affixed to the support at a different and discreet location on the support. Preferred are supports wherein 256 different compositions are distributed in a preselected array.

G. Methods for sequencing by Hybridization

The present invention also contemplates a solid phase method for sequencing DNA molecules by a systematic hybridization procedure utilizing the compositions of families of hexamers as defined herein. The method comprises the steps of:

(1) admixing in a hybridization reaction admixture:

a) a solid support having affixed thereto at least one family of hexamers (immobilized hexamers) as defined herein, said affixation in the orientation whereby the 5'-terminus of each hexamer is operatively linked to the support and the 3'-terminus is extending outwardly from the support and being present in the solid phase;

b) at least one composition comprising a family of hexamers as defined herein, said hexamers each having a label affixed to the hexamer and being present in the liquid phase; and c) a single stranded template nucleic acid molecule, to form a hybridization reaction admixture;

(2) treating the hybridization reaction to hybridization reaction conditions for a time period sufficient for any regions of complementarity present in said template molecule to hybridize with said liquid phase and said solid phase hexamers and form a ligation reaction substrate;

(3) treating the ligation reaction substrate to ligation reaction conditions for a time period sufficient form said substrate to be ligated, thereby forming a covalent phosphodiester bond between the 3' terminus of said solid phase hexamer and the 5' terminus of said liquid phase hexamer; and (4) determining the presence of said label in the solid phase and thereby the presence of a sequence in said template complementary to the sequence of the hexamer in the solid phase to which the label is attached.

In preferred embodiments, all 256 families of hexamers are present in the solid phase, each family affixed at a preselected position on the support. The immobilized hexamer can be operatively linked by means of a linker between the 5' terminus and the solid support.

In other embodiments, the method is carried out 256 times, each time with a different family of hexamers, such that the entire library of 256 families are independently reacted. By this method, the combination of the location of the labelled signal on the solid support and the particular liquid phase family allows the determination of the presence of all possible sequences in the template. Preferably the template is 60,000 nucleotides or less in length.

EXAMPLES

The following examples are intended to illustrate, but not limit, the present invention.

1. Oligonucleotide Synthesis

The oligonucleotides in these Examples were synthesized on an Applied Biosystems Inc. (ABI) DNA synthesizer, model 391 or 392, with ABI reagents at a 0.2 um scale using standard cyanoethyl phosphoramidite chemistry and deprotection protocols according to the manufacturer's instructions.

The hexamers were chemically phosphorylated at their 5'-end by the addition, and subsequent deprotection of, 1-Dimethoxytrityl-2, 2'-sulfonyldiethanol-1-CED™ phosphoramidite (ABI).

The crude hexamers were purified by PAGE and then desalted and lyophilized by standard procedures.

The nucleotide (base) positions which vary between members of each hexamer family designated by "N" were generated by equimolar mixing of the phosphoramidite bases (A, G, C T) on-line within the synthesizer following manufacturer's instructions to form a family (pool) of hexamers.

The oligonucleotides used in these Examples are described in Tables 1 and 2:

TABLE 1

| Template No. | N-mer | Sequence (ID No): |
| --- | --- | --- |
| 1 | 8 | 5' TGGCCGTC 3' |
| 2 | 10 | (1) CTGGCCGTCG |
| 3 | 12 | (2) ACTGGCCGTCGT |
| 4 | 16 | (3) TCACTGGCCGTCGTTT |
| 5 | 16 | (4) TCGCTGGCCGTCGGTT |
| 6 | 16 | (5) TCACTGGCCGTCGATT |
| 7 | 16 | (6) TCCCTGGCCGTCGCTT |
| 8 | 16 | (7) TCGCTGGCCGTCGGTT |
| 9 | 16 | (8) TCTCTGGCCGTCGTTT |
| 10 | 16 | (9) TCACTNGCCGTNGTTT |

TABLE 2

| Oligo No. | n-mer | Sequence (ID No): |
| --- | --- | --- |
| 1B | 6 | 3' TGACCG5' |
| *2A | 6 | GCAGCA |
| 3B | 5 | GACCG |
| 4A | 5 | GCAGC |
| 5B | 6 | AGACCG |
| *6A | 6 | GCAGCA |
| 7B | 6 | CGACCG |
| 8A | 6 | GCAGCC |
| 9B | 6 | GGACCG |
| 10A | 6 | GCAGCG |
| 11B | 6 | TGNCCG |
| 12A | 6 | GCNGCA |
| 13A | 12 | (10) GCAGCATGGATT |
| 14B | 12 | (11) TCACTTAGACCG |
| 15B | 6 | TGACCN |
| 16A | 6 | GCAGCN |
| 17B | 6 | TGACNN |
| 18A | 6 | GCAGNN |
| 19B | 6 | GGTANN |
| 20A | 6 | GGGANN |

*Oligonucleotide 2A and Oligonucleotide 6A are of the same sequence

2. Sequencing of Template Using Hexamers

The hexamers were used to sequence single-stranded (ss) M13mp7 and double-stranded pBluescript. Prior to sequencing, ligation reactions were performed to demonstrate that the hexamers would ligate to form a 12-mer.

a. M13mp7 Sequencing

A ligation reaction admixture was formed by combining 5 ul ssM13mp7 (1 ug; Stratagene, La Jolla, Calif.), 1 ul kinased Oligo 1B (50 ng; see Example 1 for sequence and synthesis), 1 ul Oligo 2A (50 ng; see Example 1), 1 ul rATP (10mM; Stratagene, La Jolla, CA), and 10 ul 10X ligase buffer. Oligo 1B was kinased according to the method in Example 3. 10X ligase buffer is 50mM Tris-HCl pH7.5, 7mM $MgCl_2$, 1 mM DDT (dithiothreitol). The mixture was allowed to incubate at 65° C. in a water bath for 10 min, and was then slowly cooled to either 4, 14, or 22° C. and maintained at those temperatures during ligation. When the reaction reached the desired temperature 5 units of T4 DNA ligase (Stratagene, La Jolla, Calif.) were added, and the reaction was maintained at the indicated temperatures for 60 minutes to form a ligated primer. Next, the mixture was incubated in a water bath at 72° C. for two min in the presence of 1 ul Sequenase Stop buffer (90% formamide, 0.25% bromphenol blue, and 0.25% xylene cyanol; U.S. Biochemicals, N.J.). A 40 cm, 20% acrylamide (19:1, acrylamide: bisacrylamide), 7M urea gel was prepared in 1X TBE. Prior to sample loading the gel was run for 1 hr at 75 Watts. Aliquots of samples and standards (a pool of 6-,12-, and 17-mers kinased with [$^{32}$P]-gamma-ATP according to Example 3) were then loaded into individual lanes and the gel was run at the same settings as noted above until the bromphenol blue migrated approximately 28 cm.

The resulting gel is shown in FIG. 1. The data indicate that the two 6-mer oligos ligated to form a 12-mer at ligation reaction temperatures of 4°, 14°, or 22° C.

To begin the sequencing reaction, the ligation mixture containing ligated primer formed in the 4° C. ligation was incubated at 65° C. for 10 min to denature the template from the oligonucleotides or from the primer, and then slowly cooled to 30° C., at which temperature only 12-mer ligation products will anneal to the template. Standard Sequenase 2.0 (US Biochemicals, N.J.) labeling/termination reactions were then performed following manufacturer's instructions. The sequencing reaction was then run on a 6% sequencing gel following standard procedures.

The results of the sequencing reaction are shown in FIG. 1. High-level resolution of M13mp7 nucleotide bases were achieved by the hexamer primerbased sequencing.

b. pBluescript Sequencing

Three different pairs of hexamer compositions, each member containing 0, one, or two variable bases with respect to the pBluescript template, were used to sequence a segment of pBluescript plasmid DNA. The pairs of hexamer containing variable nucleotides (N) were added as pools; each member of the pool represented one of the four or sixteen possible oligo sequences. Prior to sequencing, ligation reactions were performed to demonstrate that the pooled oligos would ligate to form a 12-mer.

The double-stranded pBluescript plasmid (Stratagene, La Jolla, Calif.) was made single-stranded by denaturation. The denaturation reaction contained 5 ul pBluescript (5 ug), 2 ul 2M NaOH, 2 ul 2mM EDTA, and 11 ul $H_2O$ (double distilled and autoclaved), and was incubated at 65° C. for 5 min. Following the short incubation, 8 ul 5M NH40AC and 50 ul EtOH were added and the mixture was incubated for 10 min at 4° C. The reaction was then spun at 14K for 10 min at 4° C. The supernatant was discarded and the pellet was washed with 100 ul of 70% EtOH.

To begin the ligation reaction, the denatured pellet was combined with 1 ul 10X ligase buffer, 1 ul 10mM rATP, 5 ul $H_2O$, and Oligo A and Oligo B. The quantities of Oligo A and B (Oligo B was kinased according to method in Example 3) were as follows:

| Oligo Pair Nos. | Quantity |
| --- | --- |
| 1B, 2A | 5 ng, 5 ng |
| 15B, 16A pools | 8 ng, 8 ng |
| 17B, 18A pools | 25 ng, 25 ng |

Figure 2:
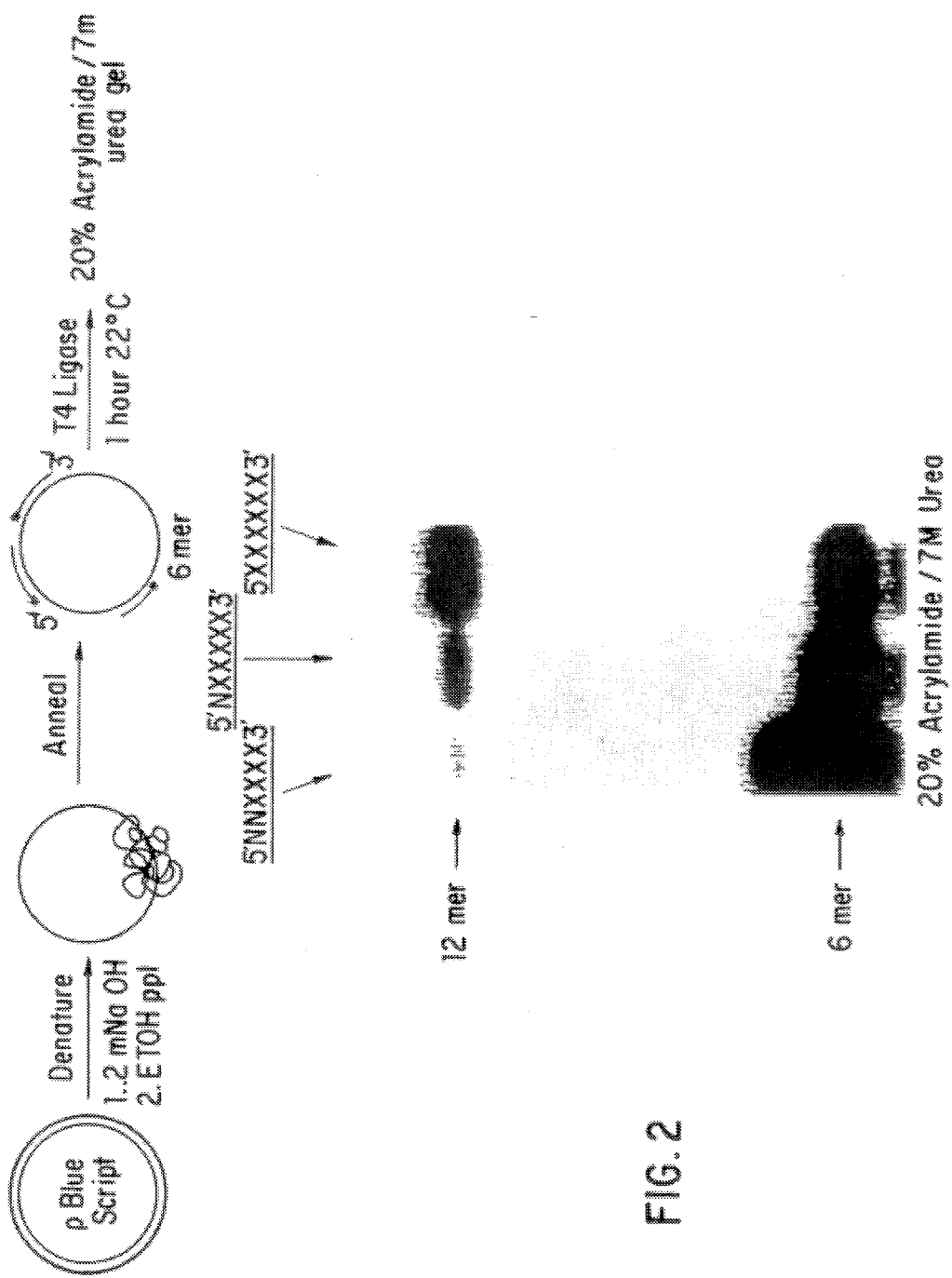
FIG. 2 illustrates separate ligation of three pairs of hexamer compositions to pBluescript plasmid DNA, as described in Example 2. The schematic diagram at the top of the Figure summarizes the steps used to effect ligation. The three pairs of hexamer compositions are designated 5'NNXXXX3', 5'NXXXXX3' and 5'XXXXXX3' to represent two, one, or no variable positions in the composition of hexamers used in each ligation reaction. The 12-mer ligation products are visualized on a 20% acrylamide/7M urea gel.

The mixtures were incubated at 100° C. for 5 min, and then slowly cooled to room temperature, which cooling took approximately 30 min. The mixtures were then incubated for 5 min at 4° C., after which time 4 units of T4 DNA ligase (Stratagene, La Jolla, Calif.) were added and the reactions were allowed to incubate at room temperature for 60 min. Next, the mixture was incubated in a water bath at 72° C. for two min in the presence of 1 ul Sequenase Stop buffer (90% formamide, 0.25% bromphenol blue, and 0.25% xylene cyanol; U.S. Biochemicals, N.J.). A 40 cm, 20% acrylamide (19:1, acrylamide:bisacrylamide), 7M urea gel was prepared in 1XTBE. Prior to sample loading the gel was run for 1 hr at 75 watts. Aliquots of samples were then loaded into individual lanes and the gel was run at the same settings as noted above until the bromphenol blue migrated 28 cm. The resulting gel is shown in FIG. 2. The data indicate that the two 6-mer oligos ligate to form a 12-mer even when two positions of variability (N) are present in both members of the hexamer pair.

The sequencing reactions were performed on the ligation reactions which used Oligos 1B/2A and Oligos 15B/16A. In addition, a ligation reaction was performed as described above with 25 ng of Oligo 19B and 25 ng of Oligo 20A. Sequencing was initiated by incubating the three ligation reactions at 100° C. for 5 min, followed by slow cooling as above to 22° C. for the 1B/2A and 15B/16A reactions, and to 22° C. or 37° C. for the 19B/20A reaction. Standard Sequenase 2.0 labeling/termination reactions were then performed following manufacturer's instructions, and the reaction products were visualized on a standard 6% sequencing gel.

Figure 3:
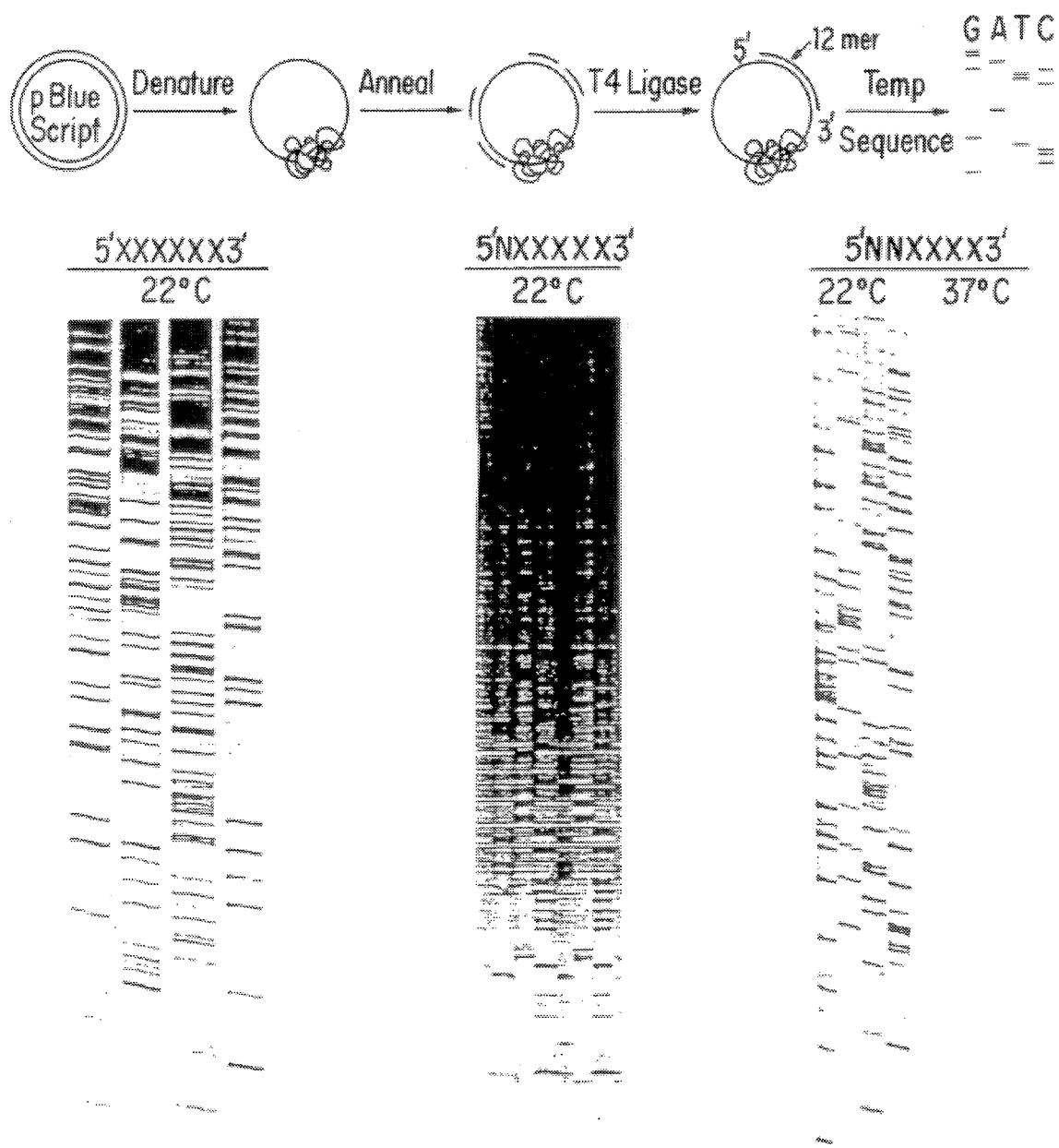
FIG. 3 illustrates a schematic representation of three pairs of hexamer compositions ligating to pBluescript plasmid DNA, and the sequencing gels resulting therefrom as described in Example 2. The three pairs of hexamer compositions are as described in FIG. 2, except that the actual sequences of the pair of hexamers designated 5'NNXXXX3' primers are as described in Example 2. The circular diagram at the top of the Figure illustrates the steps used to ligate the hexamers while hybridized to template in preparation for sequencing. The three photographs represent sequencing gels obtained using the three pairs of hexamer compositions with the sequencing primer hybridization temperatures indicated.
Figure 4A:
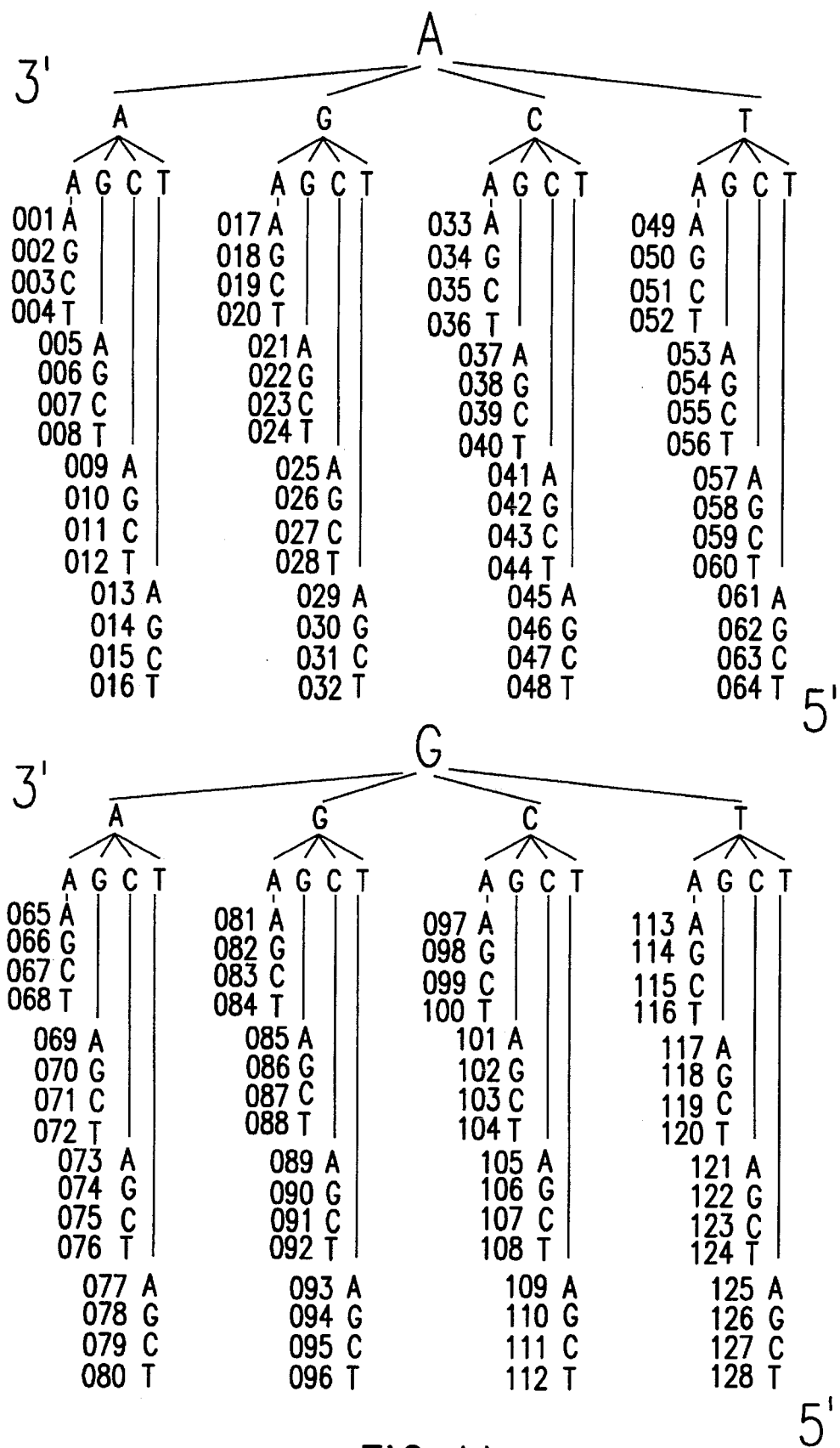
FIGS. 4A and 4B show the 256 possible 3' root 4-mers according to the formula 5'NNXXXX3'. Each 4-mer root defines a family of oligonucleotides having six nucleotide (base) positions, wherein the 4-mer root nucleotides (XXXX) form a sequence that is the same for all members of the family, and the two 5'-most nucleotides (NN, not shown) vary (independently) between members of the family. In preferred embodiments the 5'-most nucleotide in the hexamer sequence for the Oligo B is phosphorylated to facilitate directional ligation.
Figure 4B:
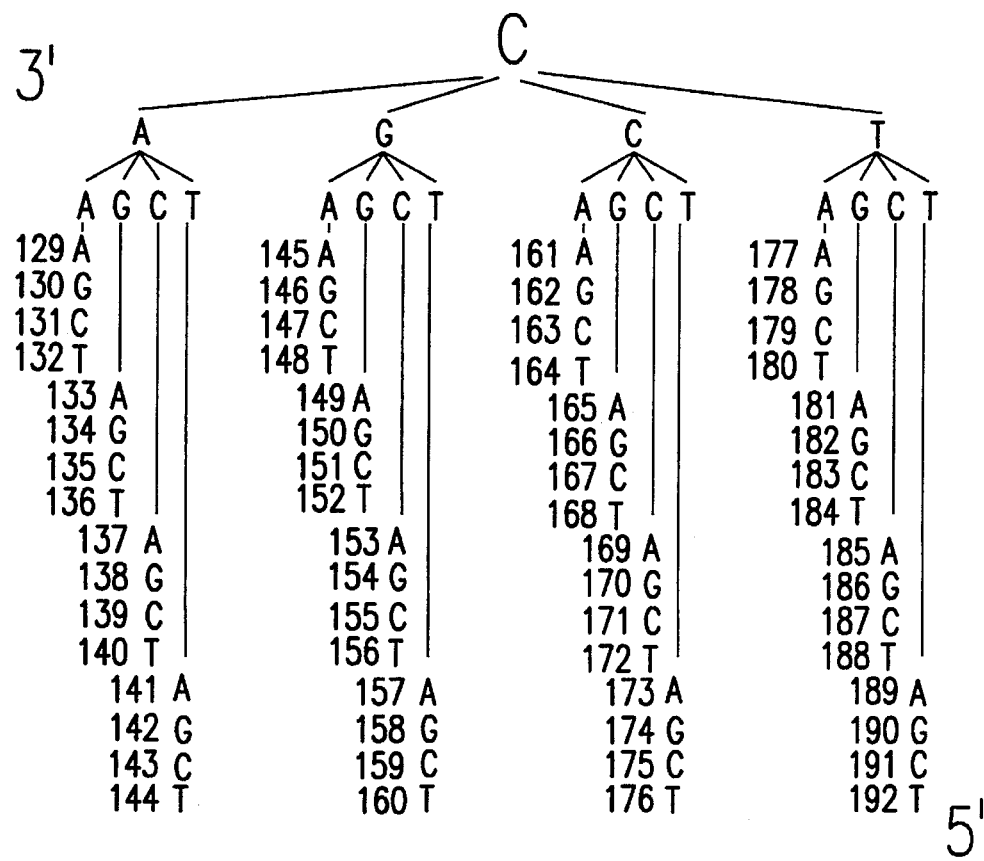
Figure 4B:
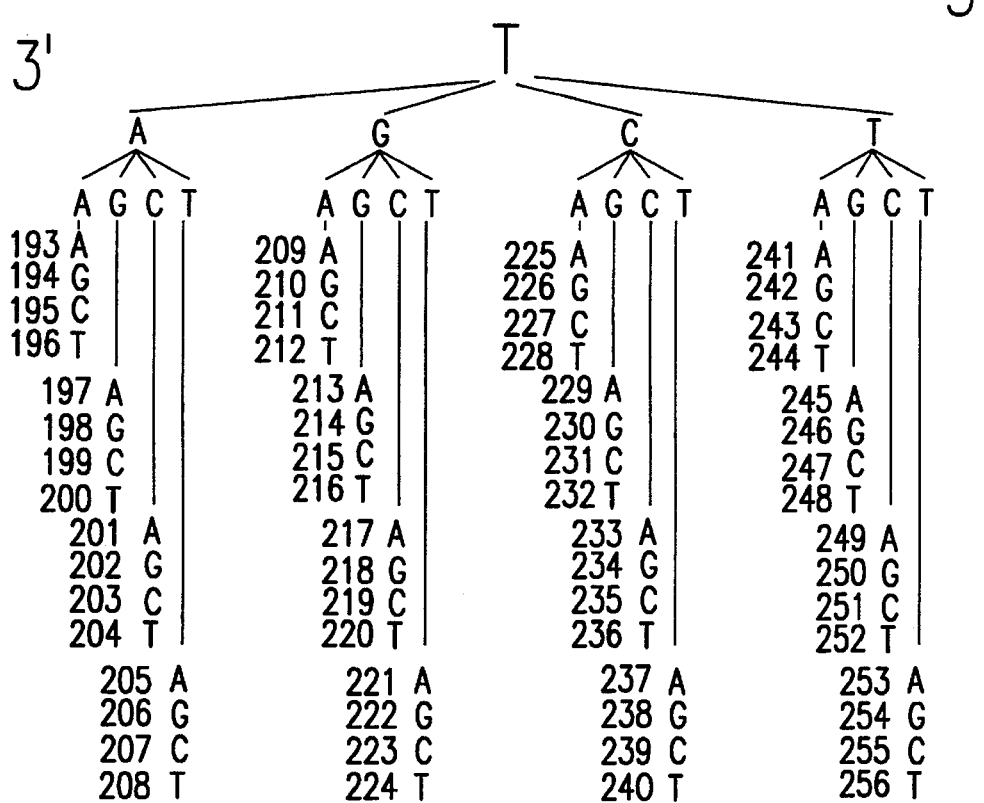

The results of the sequencing reaction are shown in FIG. 3. High-level resolution of nucleotide bases in pBluescript were achieved at 22° C. using all three of the hexamer compositions in sequencing reactions. Thus, hexamer pairs comprising members having two variable bases with respect to template can be used to sequence plasmid template at 22° C.

3. Characterization of Oligonucleotide Ligation

The following experiments were performed to elucidate various characteristics of, and requirements for, ligating oligonucleotides of the present invention while hybridized on a template nucleic acid.

The oligonucleotides used in this Example were synthesized according to the method of Example 1. The names, lengths, and sequences of these oligonucleotides are presented in Tables 1 and 2. An "A" next to the Oligo No. in Table 2 indicates that the oligo is Oligo A; a "B" indicates Oligo B.

Standard oligonucleotides of 6, 8, 10, 12, and 16 nucleotides in length also were synthesized according to the method of Example 1. The 5'-most nucleotide was phosphorylated, as described in Example 1, in all oligos used at the downstream (Oligo B) position.

Oligonucleotides were radiolabeled as needed by the following procedure. Twenty nanograms of each Primer B oligonucleotide were kinased with [$^{32}$p]gamma-ATP and T4 Polynucleotide kinase, resulting in a $^{32}$p-labeled phosphate group at the 5'-end of the primer. The kinased nucleic acid was ethanol precipitated and resuspended in sterile, deionized water using standard procedures. The oligonucleotides used as standards in these experiments also were kinased.

The ligations of this Example were initiated by annealing 20 ng kinased Oligo B, 20 ng Oligo A, and 20 ng template in 1 ul of 10X Ligase Buffer (see Example 2) and sterile, deionized water to a volume of 10 ul. Two units of T4 DNA Ligase (Stratagene, La Jolla, Calif.) were added and the mix was incubated at room temperature for 1–2 hr. The reaction was terminated by adding 1 ul Sequenase Stop buffer (90% formamide, 0.25% bromphenol blue, and 0.25% xylene cyanol; U.S. Biochemical, N.J.). A 40 cm, 20% acrylamide (19:1, acrylamide:bisacrylamide), 7M urea gel was prepared in 1X TBE. Prior to sample loading, the gel was run for 0.5 hr at 100 watts (approximately 2500 volts; approximately 64v/cm). Samples and standards were then loaded into individual lanes and the gel was run at the same setting as noted above until the bromphenol blue migrated 28 cm. Ligation was determined based on co-migration with markers.

A. Effect of Template Length on Ligation

Oligo No. 1B and Oligo No. 2A were ligated as described above to templates of 8, 10, 12, and 16 nucleotides in length, which were exact complements of the hexamers. The ligation products were then examined to determine the minimum template length to which two hexamer primers of the present invention would ligate. The results are provided in Table 3:

TABLE 3

| Template No. | Template Length (nt) | Ligation |
| --- | --- | --- |
| 1 | 8 | no |
| 2 | 10 | no |
| 3 | 12 | yes |
| 4 | 16 | yes |

These data demonstrate that the minimum length for a template strand which has exact complementarity with two hexamer oligos is 12 nucleotides for ligation of the hexamers when performed with T4 DNA Ligase.

B. Effect of Primer Length on Ligation

Oligos of either 5 or 6 nucleotides were ligated as a pair to Template No. 5, which is 16 nucleotides in length and exactly complementary to the oligos. The ligation products were examined to determine the minimum oligo length which would ligate to a 16-mer template of exact complementarity at room temperature. The results are provided in Table 4:

TABLE 4

| Oligo Nos. | Length (nt) | Ligation |
| --- | --- | --- |
| 3B, 4A | 5, 5 | no |
| 7B, 8A | 6, 6 | yes |

These data demonstrate that the minimum length for a member of a pair of oligos is 6 nucleotides when ligation of two primers to an exactly complementary template is performed with T4 DNA Ligase.

C. Effect of One Mismatch in Member of 6-mer Priming Pair

A series of ligations was performed in which the 3'-most base in Oligo B (6-mer) and the 5'-most base in Oligo A (6-mer) were not complementary to the nucleotide base found in the corresponding position of the 16-mer template. Because the primers and template were exactly complementary at all other positions, this created a mismatch at the two end bases, i.e., at bases 1 and 12 (see FIG. 5). The ligation products were examined to determine the effect of the mismatch on ligation. The results are provided in Table 5:

TABLE 5

| Oligo Nos. | Template No. | Ligation |
| --- | --- | --- |
| 5B, 6A | 6 | yes |
| 7B, 8A | 7 | yes |
| 9B, 10A | 8 | yes |
| 7B, 8A | 9 | yes |

These data demonstrate that two mismatches involving any nucleotides at positions 1 and 12 (FIG. 5), are tolerated when ligation of 6-mers to a 16-mer template is performed with T4 DNA ligase.

D. Effect of Noncentralized Ligation Point

To determine what effect, if any, a noncentralized ligation point would have on the ability of a pair of oligos to ligate while hybridized to a template, Oligos A of 5, 6, or 7 bases in length were paired with Oligos B having lengths of 5, 6, or 7 bases. The oligo pairs and template were exactly complementary except for one or two base mismatches at the 3'-most (Oligo B) or 5'-most (Oligo A) bases, i.e., positions 1 and 2 and positions 11 and 12. The results are provided in Table 6:

TABLE 6

| Length of A, B (nt) | Position of Mismatches | Ligation |
| --- | --- | --- |
| 7, 5 | 1 and 2 | no |
| 6, 5 | 1 | no |
| 6, 6 | 1 and 2; 11 and 12 | no |
| 6, 6 | 1 and 12 | yes |

These data demonstrate that 1) two oligos of at least six bases per each oligo are required to form a ligation reaction substrate, regardless of whether the 5'-most and 3'-most bases (positions 1 & 12) are mismatched with respect to template, and 2) only 5 bases per oligo are required to be ligatable, but only if the oligo is at least 6 bases in length.

E. Effect of a Pooled Family of Oligos or of Mismatched Pooled Templates on Ligation Pools of Oligo A and Oligo B are synthesized to represent each possible member of Oligo 12A and Oligo 11B, the N positions of which are occupied by A,T,G, or C. The oligo pools are then ligated to Template No. 4, which is exactly complementary to one of the four members of each of the Oligo A and Oligo B pools, and which template has one mismatch with respect to the other three members in each pool. The ligation is performed as described in this Example, except 80 ng of each Oligo pool are added to the reaction.

The ability of Oligo A and Oligo B to ligate to a pool templates where in only one in 16 of the possible templates is a perfect match is examined using a pool of Template No. 10. The ligation is performed as described in this Example, except 320 ng of template are added to the reaction. Oligo Nos. 1B and 2A are ligated to a pool of Template No. 10, the N positions of which are occupied by A,T,G, or C. All 16 possible combinations are represented in the 16 member template pool.

Pools of Oligo 12A and Oligo 11B are ligated to the pool of Template No. 10 as described in this Example, except 320 ng of the Template pool and 80 ng of each Primer pool are added to the reaction. The results of these experiments are provided in Table 7.

TABLE 7

| Template No. | Oligos | Intensity |
| --- | --- | --- |
| 4 | 12A, 11B (pools) | +++ (~16X) |
| 10 (pool) | 2A, 1B | +++ (~16X) |
| 10 (pool) | 12A, 11B (pools) | + (1X) |

These data indicate that a variable position having different nucleotides at internal base positions of a template pool or primer pool will function in a template-driven ligation reaction performed with T4 DNA Ligase.

F. Effect of Non-complementary Tail Length of Oligo on Ligation Substrate

Oligo pairs of varying lengths each pair member having five continuous (adjacent) positions of exact complementarity with templates, were examined for their ability to ligate to Template No. 8 having nucleotides. The results are provided in Table 8.

TABLE 8

| Primer Pair Nos. | Length (nt) | Mismatch Tail (nt) | Ligation |
| --- | --- | --- | --- |
| 9B, 13A | 6, 12 | 1, 7 | yes |
| 14B, 10A | 12, 6 | 7, 1 | yes |
| 14B, 13A | 12, 12 | 7, 7 | yes |

These data demonstrate that uncomplimentary tail lengths of from 1 to 7 nucleotides in length do not prevent ligation of oligos when hybridized to template.

The foregoing specification, including the specific embodiments and examples, is illustrative of the present invention and is not intended to limit the invention in any way. It will be apparent to those skilled in the art that numerous variations and modifications to the above-described embodiments of the invention will be possible without departing from the spirit and scope of the invention. It is intended that the following claims be interpreted to embrace all such variations and modifications.

What is claimed is:

1. A composition consisting essentially of a family of oligonucleotides all of the same length, said family defined by a nucleotide sequence formula containing six to eight nucleotide positions, one to three of said positions of the formula identifying positions of nucleotide variation among the family members, the remaining nucleotide positions each identifying a nucleotide that is the same in all members of the family, wherein said nucleotide is selected from the group consisting of A, T, G, C and U, wherein T and U are interchangeable.

2. A composition consisting essentially of a family of hexameric oligonucleotides, each family member having a nucleotide sequence that is different from the other family members, the family defined by a nucleotide sequence formula containing three to five constant nucleotide positions, each constant position of the sequence being occupied, independent of the other constant positions, by a nucleotide that is the same in all members of the family, the remaining nucleotide positions of the formula identifying positions of nucleotide variation among the family members, wherein said nucleotide is selected from the group consisting of A, T, G, C and U, wherein T and U are interchangeable.

3. A composition consisting essentially of a family of oligonucleotides comprising hexameric oligonucleotides, each family member having a nucleotide sequence that is different from the other family members, the family defined by a nucleotide sequence formula containing four constant and two variable positions, each constant position identifying, independent of the other constant positions, a nucleotide that is the same in all family members, wherein said nucleotide is selected from the group consisting of A, T, G, C and, wherein T and U are interchangeable.

4. The composition of claim 3 wherein said nucleotide sequence formula, read from left to right and in the direction of 5'-terminus to 3'-terminus, is:

$$N_1 X_1 X_2 X_3 X_4 N_2,$$

wherein $X_1$, $X_2$, $X_3$, and $X_4$ are the same or different nucleotide located at said four constant positions, and $N_1$ and $N_2$ are the same or different nucleotide located at said two variable positions.

5. The composition of claim 3 wherein said nucleotide sequence formula, read from left to right and in the direction of 5'-terminus to 3'-terminus, is selected from the group consisting of:

(a) $N_1 X_1 X_2 X_3 X_4 N_2,$
  (b) $N_1 N_2 X_1 X_2 X_3 X_4,$ and
  (c) $X_1 X_2 X_3 X_4 N_1 N_2,$ wherein $X_1$, $X_2$, $X_3$ and $X_4$ are the same or different nucleotide located at said four constant positions, and $N_1$ and $N_2$ are the same or different nucleotide located at said two variable positions.

6. The composition of claim 3 wherein said nucleotide sequence formula, read from left to right and in the direction of 5'-terminus to 3'-terminus, is selected from the group consisting of:

(a) $N_1 X_1 N_2 X_2 X_3 X_4,$
  (b) $N_1 X_1 X_2 N_2 X_3 X_4,$
  (c) $N_1 X_1 X_2 X_3 N_2 X_4,$ (d) $X_1 N_1 N_2 X_2 X_3 X_4$,
(e) $X_1 N_1 X_2 N_2 X_3 X_4$,
(f) $X_1 N_1 X_2 X_3 N_2 X_4$,
(g) $X_1 N_1 X_2 X_3 X_4 N_2$,
(h) $X_1 X_2 N_1 N_2 X_3 X_4$,
(i) $X_1 X_2 N_1 X_3 N_2 X_4$,
(j) $X_1 X_2 N_1 X_3 X_4 N_2$,
(k) $X_1 X_2 X_3 N_1 N_2 X_4$, and
(l) $X_1 X_2 X_3 N_1 X_4 N_2$,
wherein $X_1$, $X_2$, $X_3$ and $X_4$ are the same or different nucleotide located at said four constant positions, and $N_1$ and $N_2$ are the same or different nucleotide located at said two variable positions.

7. A composition consisting essentially of a family of oligonucleotides comprising hexameric oligonucleotides, each family member having a nucleotide sequence that is different from the other family members, the family defined by a nucleotide sequence formula containing five constant and one variable positions, each constant position identifying, independent of the other constant positions, a nucleotide that is the same in all family members, wherein said nucleotide is selected from the group consisting of A, T, G, C and U, wherein T and U are interchangeable.

8. The composition of claim 7 wherein said nucleotide sequence formula, read from left to right and in the direction of 5'-terminus to 3'-terminus, is selected from the group consisting of:

(a) $N_1 X_1 X_2 X_3 X_4 X_5$, and
(b) $X_1 X_2 X_3 X_4 X_5 N_1$, wherein $X_1$, $X_2$, $X_3$, $X_4$ and $X_5$ are the same or different nucleotides located at said five constant positions, and $N_1$ is a nucleotide located at said one variable position.

9. The composition of claim 7 wherein said nucleotide sequence formula, read from left to right and in the direction of 5'-terminus to 3'-terminus, is selected from the group consisting of:

(a) $X_1 N_1 X_2 X_3 X_4 X_5$,
(b) $X_1 X_2 N_1 X_3 X_4 X_5$,
(c) $X_1 X_2 X_3 N_1 X_4 X_5$, and
(d) $X_1 X_2 X_3 X_4 N_1 X_5$, wherein $X_1$, $X_2$, $X_3$, $X_4$ and $X_5$ are the same or different nucleotides located at said five constant positions, and $N_1$ is a nucleotide located at said one variable position.

10. The composition of claim 3 or 7 wherein the members of the family are present in relative molar amounts such that any one member is present in no more than a ten-fold excess of the amount of the least abundant member.

11. The composition of claim 3 or 7 wherein the members of the family are present in equimolar amounts.

12. The composition of claim 7 wherein the nucleotide formula, read from left to right and in the direction of 5'-terminus to 3'-terminus, is selected from the group consisting of:

(a) $N_1 X_1 X_2 X_3 X_4 X_5$, and
(b) $X_1 X_2 X_3 X_4 X_5 N_1$, wherein $X_1$, $X_2$, $X_3$, $X_4$ and $X_5$ are the same or different nucleotide located at said five constant positions, with the proviso that at least two of $X_1$, $X_2$, $X_3$, $X_4$ and $X_5$ are the nucleotides G or C, and $N_1$ is a nucleotide located at said one variable position.

13. The composition of claim 12 wherein the family of oligonucleotides is represented by the formula:

$$N_1 X_1 X_2 X_3 X_4 X_5$$

wherein $X_4$ and $X_5$ are the nucleotides G or C.

14. The composition of claim 12 wherein the family of oligonucleotides is represented by the formula:

$$X_1 X_2 X_3 X_4 X_5 N_1$$

wherein $X_1$ and $X_2$ are the nucleotides G or C.

15. A kit for producing a dodecameric oligonucleotide of preselected priming specificity, which kit comprises a plurality of separate packages within an enclosure, each package containing a different hexameric oligonucleotide composition, said composition consisting essentially of a family of hexameric oligonucleotides, each family member having a nucleotide sequence that is different from the other family members, the family defined by a nucleotide sequence formula containing four constant and two variable positions, each constant position identifying, independent of the other constant positions, a nucleotide that is the same in all family members, the hexameric oligonucleotides of each composition being adapted for ligation to any one of the hexameric oligonucleotides in each of the other packages to produce said dodecameric oligonucleotide, wherein said nucleotide is selected from the group consisting of A, T, G, C and U, wherein T and U are interchangeable.

* * * * *